US012644112B2

(12) United States Patent
Sun et al.

(10) Patent No.: US 12,644,112 B2
(45) Date of Patent: *Jun. 2, 2026

(54) T7 DNA LIGASE VARIANTS WITH INCREASED LIGATION ACTIVITY

(71) Applicant: AbClonal Science, Inc., Woburn, MA (US)

(72) Inventors: Dapeng Sun, Lexington, MA (US); Zhenyu Zhu, Lynnfield, MA (US); Aine Quimby, Newburyport, MA (US)

(73) Assignee: ABCLONAL SCIENCE INC., Woburn, MA (US)

( * ) Notice: Subject to any disclaimer, the term of this patent is extended or adjusted under 35 U.S.C. 154(b) by 195 days.

This patent is subject to a terminal disclaimer.

(21) Appl. No.: 18/418,225

(22) Filed: Jan. 20, 2024

(65) Prior Publication Data

US 2025/0236860 A1      Jul. 24, 2025

(51) Int. Cl.
*C12N 9/00*      (2006.01)
*C12P 19/34*      (2006.01)

(52) U.S. Cl.
CPC ................ *C12N 9/93* (2013.01); *C12P 19/34* (2013.01); *C12Y 605/01001* (2013.01)

(58) Field of Classification Search
CPC .... C12N 9/93; C12P 19/34; C12Y 605/01001
See application file for complete search history.

(56) References Cited

U.S. PATENT DOCUMENTS

| | | |
|---|---|---|
| 10,920,202 B1 | 2/2021 | Zhu et al. |
| 10,947,518 B1 | 3/2021 | Zhu et al. |
| 11,020,474 B1 | 6/2021 | Xiang et al. |
| 2020/0283825 A1 | 9/2020 | Zhu et al. |
| 2020/0291455 A1 | 9/2020 | Zhu et al. |
| 2020/0362320 A1 | 11/2020 | Zhu et al. |
| 2021/0079365 A1 | 3/2021 | Zhu et al. |
| 2021/0087550 A1 | 3/2021 | Zhu et al. |
| 2021/0171925 A1 | 6/2021 | Zhu et al. |
| 2021/0403537 A1 | 12/2021 | Xiang et al. |
| 2022/0064266 A1 | 3/2022 | Xiang et al. |
| 2022/0106576 A1 | 4/2022 | Zhu et al. |
| 2023/0033390 A1 | 2/2023 | Xiang |
| 2023/0094503 A1 | 3/2023 | Zhu et al. |
| 2023/0111383 A1 | 4/2023 | Zhu et al. |
| 2023/0212550 A1 | 7/2023 | Zhu et al. |
| 2023/0265412 A1 | 8/2023 | Zhu et al. |
| 2023/0295707 A1 | 9/2023 | Zhu et al. |
| 2024/0052326 A1 | 2/2024 | Zhu et al. |
| 2024/0067951 A1 | 2/2024 | DiCicco et al. |
| 2024/0124854 A1 | 4/2024 | Zhu et al. |
| 2024/0247246 A1* | 7/2024 | Sun .......................... C12N 9/93 |
| 2024/0279626 A1 | 8/2024 | Sun et al. |
| 2024/0392264 A1 | 11/2024 | Zhu et al. |
| 2024/0392267 A1 | 11/2024 | Zhu et al. |
| 2024/0392276 A1 | 11/2024 | Sun et al. |
| 2024/0392336 A1 | 11/2024 | Sun et al. |
| 2025/0051739 A1 | 2/2025 | Zhu et al. |
| 2025/0223574 A1 | 7/2025 | Zhu et al. |
| 2025/0236860 A1 | 7/2025 | Sun et al. |

* cited by examiner

*Primary Examiner* — Tekchand Saidha
(74) *Attorney, Agent, or Firm* — Eric P. Mirabel

(57) ABSTRACT

The invention includes a mutant T7 DNA ligase or a biologically active fragment thereof, which has greater activity than wild type T7 DNA ligase. The mutant T7 DNA ligase, or the biologically active fragment, has one or more substitutions differing from the wild type, as described more fully in the Summary. The preferred mutant T7 DNA ligase has at least one of the following mutations: E63K (SEQ ID NO:4), K73E (SEQ ID NO:6), K137E (SEQ ID NO:7), K174E (SEQ ID NO:9), E182K (SEQ ID NO:11), K210E (SEQ ID NO: 13), E243K (SEQ ID NO:15), D245R (SEQ ID NO: 17), E268K (SEQ ID NO:19), E272K (SEQ ID NO:21), E289K (SEQ ID NO:23), K295E (SEQ ID NO:25) and D336R (SEQ ID NO:27).

4 Claims, 1 Drawing Sheet

Specification includes a Sequence Listing.

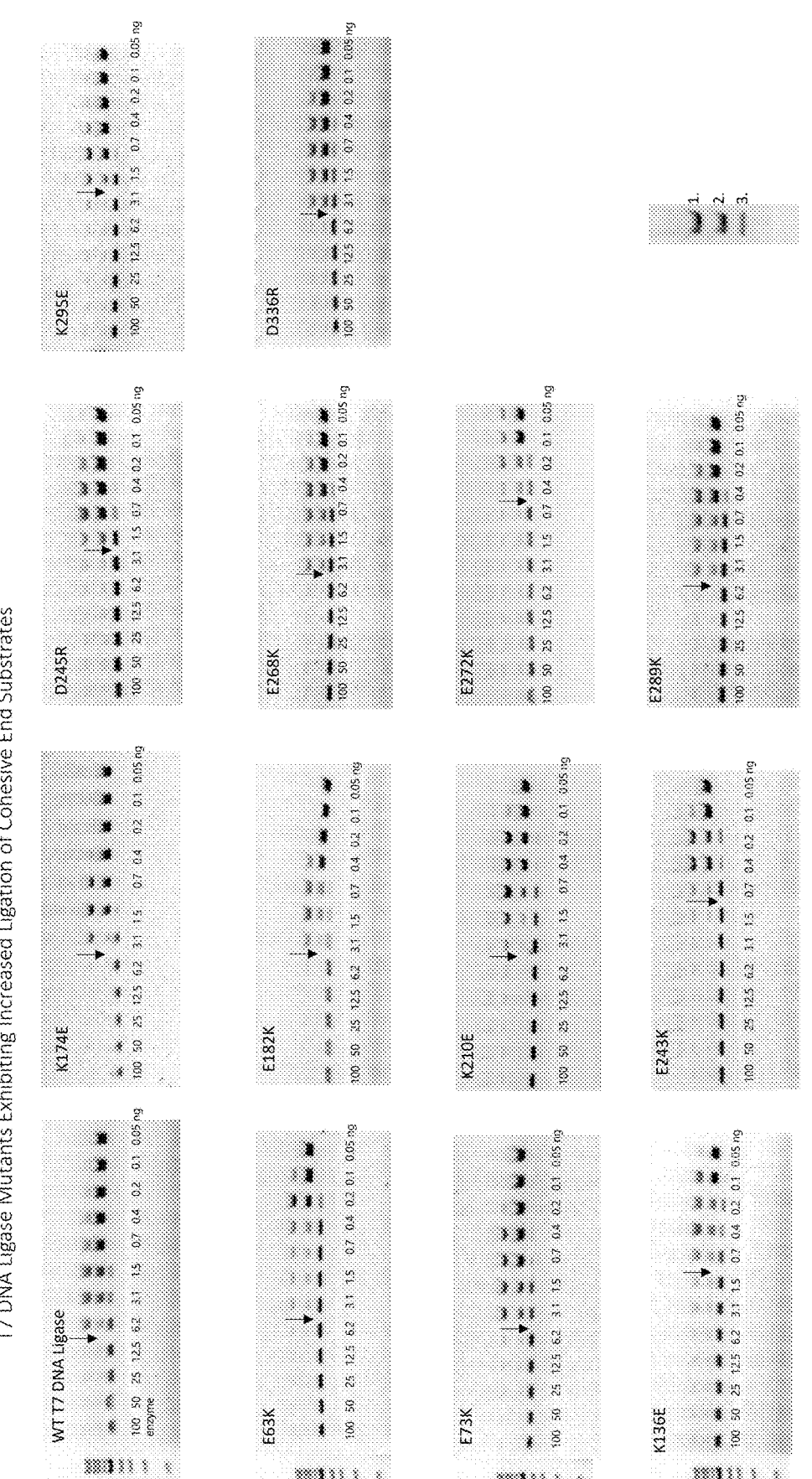
T7 DNA Ligase Mutants Exhibiting Increased Ligation of Cohesive End Substrates

T7 DNA LIGASE VARIANTS WITH INCREASED LIGATION ACTIVITY

2. The instant application contains a Sequence Listing which has been submitted electronically in XML file format and is hereby incorporated by reference in its entirety. Said XML copy, was created on 22 Jan. 2024, is named ID 1366_Seq Listing, and is 50000 bytes in size.

BACKGROUND

Ligases are commonly used in molecular biology for forming phosphodiester bonds between duplex nucleic acid fragments at the intersection of juxtaposed 5' phosphate and 3' hydroxyl termini. By designing complementary overhangs between each of the double-stranded fragments, ligation can be directed to be both positionally specific and directionally oriented. This allows for specific integration of DNA or RNA fragments into larger vectors to meet the needs of molecular biology research. T7 DNA Ligase is a thermostable ATP-dependent enzyme that efficiently catalyzes the bond joining double-stranded DNA polynucleotides displaying cohesive ends longer than a singular overhanging base. Also, it can repair via ligation the mismatches that exist in nicked DNA.

Ligases are the backbone of many molecular biology protocols, enabling users to design and connect various nucleotide molecules for uses such as cloning, protein expression, and sequencing. Increasing the inherent ligation activity of T7 DNA ligase magnifies the usefulness of the enzyme, allowing for ligations that requiring less enzyme or less total time for a complete ligation of substrates, depending on the goal of the user.

Conventionally, ligases are a molecular cloning tool used to insert specific DNA fragments into vectors prior to transformation into competent cells, for ligation of sequencing adaptors as part of NGS workflows, or as part of various other molecular biology protocols that require joining two or more segments of double-stranded DNA polynucleotides. DNA polynucleotides are considered to have blunt ends when they do not contain unpaired bases at either 3' or 5' termini, compared to sticky-ends in which overhanging bases extend from the ends of a segment, and these overhangs can provide sites for complementary DNA binding and ligation.

T7 DNA ligase is an ATP-dependent enzyme from bacteriophage that can catalyze phosphodiester bonds between two complementary overhanging ends of double-stranded DNA fragments, effectively joining the two separate DNA fragments together. T7 DNA Ligase can also repair mismatches that exist in nicked DNA through esterification of the 5'-phosphoryl group to a 3'-hydroxyl group. Additionally, however, that ligation of double-stranded DNA substrates with blunt ends is possible in the presence of crowding agents such as polyethylene glycol (PEG). PEG is also used to increase the overall activity of T7 DNA ligase up to 100-fold over standard activity, and is a common additive to ligase buffers.

SUMMARY

The invention relates to a mutant T7 DNA ligase exhibiting enhanced ligation activity compared to the wild-type ligase. The following T7 DNA ligase mutants, followed by their amino acid sequence number identifiers, were identified as having such enhanced ligation activity: E63K (SEQ ID NO:4), K73E (SEQ ID NO:6), K137E (SEQ ID NO:7), K174E (SEQ ID NO:9), E182K (SEQ ID NO:11), K210E (SEQ ID NO: 13), E243K (SEQ ID NO:15), D245R (SEQ ID NO: 17), E268K (SEQ ID NO:19), E272K (SEQ ID NO:21), E289K (SEQ ID NO:23), K295E (SEQ ID NO: 25) and D336R (SEQ ID NO:27).

The invention further includes mutant T7 DNA ligase amino acid sequences with at least one of the mutations above, but wherein the remainder of the T7 DNA ligase mutant amino acid sequence only has conservative substitutions such that the molecule has at least 70%, 80%, 90%, 95%, 96%, 97%, 98% or 99% identity to the corresponding T7 DNA ligase mutant amino acid sequence in the sequence listing (hereinafter referred to as "Variant Sequences").

The invention further includes the DNA sequences preceding the amino acid sequences for the mutants above (i.e., respectively, SEQ ID NOS: 3; 5; 8; 10; 12; 14; 16; 18; 20; 22; 24; 26) and further includes the foregoing DNA sequences and other degenerate nucleic acid sequences (collectively the "Degenerate Nucleic Acid Sequences") encoding (i) each of the above T7 DNA ligase mutants, and (ii) the amino acid sequences of any of the Variant Sequences.

The invention further includes vectors incorporating any Degenerate Nucleic Acid Sequences; and cells transformed with any such vectors or Degenerate Nucleic Acid Sequences and capable of expressing any of the above T7 DNA ligase mutant amino acid sequences or Variant Sequences.

The invention further includes a composition or a kit comprising any of the above T7 DNA ligase mutant amino acid sequences or Variant Sequences, Degenerate Nucleic Acid Sequences, or vectors incorporating such Degenerate Nucleic Acid Sequences. The invention also includes a process of amplifying a target nucleic acid, wherein any of the above T7 DNA ligase mutants or Variant Sequences are employed in a reaction mixture designed to amplify a target nucleic acid, and subjecting the reagent mixture to conditions for amplification of the target nucleic acid.

The above mutant T7 DNA ligases have greater activity in ligation of cohesive end substrates (polynucleotides) at lower concentrations compared with wild type, and the Variant Sequences are also expected to have such greater activity. The above mutant T7 DNA ligases can be used in sequencing methods, including, in attaching adapters to library fragments for subsequent sequencing; or in generating oligonucleotides with regions for sequencing, following replication in plasmids.

Additional aspects and advantages of the present disclosure will become apparent to those skilled in this art from the following detailed description and drawings, wherein only illustrative embodiments of the present disclosure are shown and described. The present disclosure is capable of other and different embodiments, and several details are capable of modifications in various obvious respects, and its several details are capable of modifications in various obvious respects, all without departing from the disclosure. Accordingly, the descriptions, and examples in this summary are intended for purposes of illustration only and are not intended to limit the scope of the present disclosure.

BRIEF DESCRIPTION OF THE DRAWINGS

FIG. 1 shows a series of gel electrophoresis results from an activity assay of the wild type T7 DNA ligase ("WT" at top left) compared with each of the T7 DNA ligase mutants. There are 12 columns in each gel, such that left to right, each column represents the concentration of T7 DNA ligase following a 1:2 serial dilution, and wherein in column 1, there was 100 ng of T7 DNA Ligase (or mutant) initially present in the solution. Each gel has an arrow at the dilution level where significant amounts of ligated product are apparent. Three bands delineate the substrate from the products; supercoiled plasmid product (upper band, labeled "1" on right) and restriction digested linearized substrate plasmid (middle band, labeled "2" on right), and final product (the lowermost band, labeled "3" on right) which is the open-circle plasmid product ligated by the T7 DNA ligase wild type or the mutant indicated.

DETAILED DESCRIPTION

The embodiments herein and the various features and advantageous details thereof are explained more fully with reference to the non-limiting embodiments that are illustrated in the accompanying drawings and the following description. Numerous variations, changes, and substitutions may occur to those skilled in the art without departing from the invention. It should be understood that various alternatives to the embodiments of the present disclosure herein may be employed.

At the outset, for ease of reference, certain terms used in this application and their meanings as used in this context are set forth. To the extent a term used herein is not defined below, it should be given the broadest definition persons in the pertinent art have given that term as reflected in at least one printed publication or issued patent. Further, the present techniques are not limited by the usage of the terms shown below, as all equivalents, synonyms, new developments, and terms or techniques that serve the same or a similar purpose are considered to be within the scope of the present claims.

The articles "a" and "an" as used herein mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

The term "biologically active fragment" refers to any fragment, derivative, homolog or analog of a T7 DNA ligase mutant that possesses in vivo or in vitro activity that is characteristic of that biomolecule; including, for example, ligase activity or repairing via ligation the mismatches that exist in nicked DNA. In some embodiments, the biologically active fragment, derivative, homolog or analog of the mutant T7 DNA ligase possesses any degree of the biological activity of the mutant T7 DNA ligase in any in vivo or in vitro assay of interest.

In some embodiments, the biologically active fragment can optionally include any number of contiguous amino acid residues of the mutant T7 DNA ligases. The invention also includes the polynucleotides encoding any such biologically active fragment.

Biologically active fragments can arise from post transcriptional processing or from translation of alternatively spliced RNAs, or alternatively can be created through engineering, bulk synthesis, or other suitable manipulation. Biologically active fragments include fragments expressed in native or endogenous cells as well as those made in expression systems such as, for example, in bacterial, yeast, plant, insect or mammalian cells.

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) supra). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

When referring to a gene, "mutant" means the gene has at least one base (nucleotide) change, deletion, or insertion with respect to a native or wild type gene. The mutation (change, deletion, and/or insertion of one or more nucleotides) can be in the coding region of the gene or can be in an intron, 3' UTR, 5' UTR, or promoter region. As nonlimiting examples, a mutant gene can be a gene that has an insertion within the promoter region that can either increase or decrease expression of the gene; can be a gene that has a deletion, resulting in production of a nonfunctional protein, truncated protein, dominant negative protein, or no protein; or, can be a gene that has one or more point mutations leading to a change in the amino acid of the encoded protein or results in aberrant splicing of the gene transcript.

The terms "mutant T7 DNA ligase of the invention" and "mutant T7 DNA ligase" when used in this Detailed Description section refer to, depending on the context, collectively or individually, the mutant T7 DNA Ligase polypeptides tested and exhibiting enhanced ligation activity which are: E63K, K73E, K137E, K174E, E182K, K210E, E243K, D245R, E268K, E272K, E289K, K295E, and D336R; and/or Variant Sequences and/or Degenerate Nucleic Acid Sequences, as those terms are defined in the Summary section.

"Naturally-occurring" or "wild-type" refers to the form found in nature. For example, a naturally occurring or wild-type polypeptide or polynucleotide sequence is a sequence present in an organism, which has not been intentionally modified by human manipulation.

The terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), Nature Genetics 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), Proc. Natl. Acad. Sci. USA 89, 10915-10919), recommended for query sequences over 85 units in length (nucleotide bases or amino acids).

In some embodiments, the invention relates to methods (and related kits, systems, apparatuses and compositions) for performing a ligation reaction comprising or consisting of contacting a mutant T7 DNA ligase or a biologically active fragment thereof with a nucleic acid template in the presence of one or more nucleotides, and ligating at least one of the one or more nucleotides using the mutant T7 DNA ligase or the biologically active fragment thereof.

In some embodiments, the method can include ligating a double stranded DNA polynucleotide strand into a circular molecule. In some embodiments, the method can further include detecting a signal indicating the ligation by using a sensor. In some embodiments, the sensor is an ISFET. In some embodiments, the sensor can include a detectable label or detectable reagent within the ligating reaction.

In some embodiments, the invention relates to methods (and related kits, systems, apparatus and compositions) for performing rolling circle amplification (see U.S. Pat. No. 5,714,320, incorporated by reference) of a nucleic acid, using the mutant T7 DNA ligase as the enzyme in the ligation steps of the amplification process. The amplifying includes amplifying nucleic acid in solution, as well as clonally amplifying the nucleic acid on a solid support such as a nucleic acid bead, flow cell, nucleic acid array, or wells present on the surface of the solid support.

Making Mutant T7 DNA Ligase

The mutant T7 DNA ligase of the invention can be expressed in any suitable host system, including a bacterial, yeast, fungal, baculovirus, plant or mammalian host cell. For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proc. Natl Acad. Sci. USA 75:3727-3731), as well as the tac promoter (DeBoer et al., 1983, Proc. Natl Acad. Sci. USA 80:21-25).

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

For baculovirus expression, insect cell lines derived from Lepidopterans (moths and butterflies), such as *Spodoptera frugiperda*, are used as host. Gene expression is under the control of a strong promoter, e.g., pPolh.

Plant expression vectors are based on the Ti plasmid of *Agrobacterium tumefaciens*, or on the tobacco mosaic virus (TMV), potato virus X, or the cowpea mosaic virus. A commonly used constitutive promoter in plant expression vectors is the cauliflower mosaic virus (CaMV) 35S promoter.

For mammalian expression, cultured mammalian cell lines such as the Chinese hamster ovary (CHO), COS, including human cell lines such as HEK and HeLa may be used to produce the mutant T7 DNA ligase. Examples of mammalian expression vectors include the adenoviral vectors, the pSV and the pCMV series of plasmid vectors, vaccinia and retroviral vectors, as well as baculovirus. The promoters for cytomegalovirus (CMV) and SV40 are commonly used in mammalian expression vectors to drive gene expression. Non-viral promoters, such as the elongation factor (EF)-1 promoter, are also known.

The control sequence for the expression may also be a suitable transcription terminator sequence, that is, a sequence recognized by a host cell to terminate transcription. The terminator sequence is operably linked to the 3' terminus of the nucleic acid sequence encoding the polypeptide. Any terminator which is functional in the host cell of choice may be used.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase.

Terminators for insect, plant and mammalian host cells are also well known.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiol Rev 57:109-137.

Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Signal peptides for other host cell systems are also well known.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the mutant T7 DNA ligase relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter. Regulatory systems for other host cells are also well known.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the KRED polypeptide of the present invention would be operably linked with the regulatory sequence.

Another embodiment includes a recombinant expression vector comprising a polynucleotide encoding an engineered mutant T7 DNA ligase or a variant thereof, and one or more expression regulating regions such as a promoter and a terminator, and a replication origin, depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the mutant T7 DNA ligase at such sites. Alternatively, the nucleic acid sequences of the mutant T7 DNA ligase may be expressed by inserting the nucleic acid sequences or a nucleic acid construct comprising the sequences into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the mutant T7 DNA ligase polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector herein preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*. Selectable markers for insect, plant and mammalian cells are also well known.

The expression vectors of the present invention preferably contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location (s) in the chromosome(s). The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A ori, or the origins of replication of plasmids pBR322, pUC19, pACYC177 (which plasmid has the P15A ori), or pACYC184 permitting replication in *E. coli*, and pUB110, pE194, pTA1060, or pAM31 permitting replication in *Bacillus*. Examples of origins of replication for use in a yeast host cell are the 2 micron origins of replication, ARS1, ARS4, the combination of ARS1 and CEN3, and the combination of ARS4 and CEN6. The origin of replication may be one having a mutation which makes it's functioning temperature-sensitive in the host cell (see, e.g., Ehrlich, 1978, Proc Natl Acad Sci. USA 75:1433).

More than one copy of a nucleic acid sequence of the mutant T7 DNA ligase may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Expression vectors for the mutant T7 DNA ligase polynucleotide are commercially available. Suitable commercial expression vectors include p3×FLAG™ expression vectors from Sigma-Aldrich Chemicals, St. Louis Mo., which includes a CMV promoter and hGH polyadenylation site for expression in mammalian host cells and a pBR322 origin of replication and ampicillin resistance markers for amplification in *E. coli*. Other suitable expression vectors are pBluescriptII SK(−) and pBK-CMV, which are commercially available from Stratagene, LaJolla Calif., and plasmids which are derived from pBR322 (Gibco BRL), pUC (Gibco BRL), pREP4, pCEP4 (Invitrogen) or pPoly (Lathe et al., 1987, Gene 57:193-201).

Suitable host cells for expression of a polynucleotide encoding the mutant T7 DNA ligase, are well known in the art and include but are not limited to, bacterial cells, such as *E. coli, Lactobacillus kefir, Lactobacillus brevis, Lactobacillus minor, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art.

Polynucleotides for expression of the mutant T7 DNA ligase may be introduced into cells by various methods known in the art. Techniques include among others, electroporation, biolistic particle bombardment, liposome mediated transfection, calcium chloride transfection, and protoplast fusion. Various methods for introducing polynucleotides into cells are known to the skilled artisan.

Polynucleotides encoding the mutant T7 DNA ligase can be prepared by standard solid-phase methods, according to known synthetic methods. In some embodiments, fragments of up to about 100 bases can be individually synthesized, then joined (e.g., by enzymatic or chemical ligation methods, or polymerase mediated methods) to form any desired continuous sequence. For example, polynucleotides can be prepared by chemical synthesis using, e.g., the classical phosphoramidite method described by Beaucage et al., 1981, Tet Lett 22:1859-69, or the method described by Matthes et al., 1984, EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, such as The Midland Certified Reagent Company, Midland, Tex., The Great American Gene Company, Ramona, Calif., ExpressGen Inc. Chicago, Ill., and Operon Technologies Inc., Alameda, Calif.

Engineered mutant T7 DNA ligase expressed in a host cell can be recovered from the cells and or the culture medium using any one or more of the well-known techniques for protein purification, including, among others, lysozyme treatment, sonication, filtration, salting-out, ultra-centrifugation, and chromatography. Suitable solutions for lysing and the high efficiency extraction of proteins from bacteria, such as E. coli, are commercially available under the trade name CelLytic B™ from Sigma-Aldrich of St. Louis Mo.

Chromatographic techniques for isolation of the mutant T7 DNA ligase include, among others, reverse phase chromatography high performance liquid chromatography, ion exchange chromatography, gel electrophoresis, and affinity chromatography. Conditions for purification will depend, in part, on factors such as net charge, hydrophobicity, hydrophilicity, molecular weight, molecular shape, and will be apparent to those having skill in the art.

In some embodiments, affinity techniques may be used to isolate the mutant T7 DNA ligase. For affinity chromatography purification, any antibody which specifically binds the mutant T7 DNA ligase may be used. For the production of antibodies, various host animals, including but not limited to rabbits, mice, rats, etc., may be immunized by injection with a compound. The compound may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum*.

Example of Making T7 DNA Ligase Mutants

T7 DNA ligase mutants were generated by conventional PCR mutagenesis wherein the primers are designed to include the desired base substitution, and during PCR, the mutation is incorporated into the amplicon, replacing the original sequence. The T7 DNA ligase mutants and the wild type preferably has an added C-terminal 6-mer His tag for ease of purification, preceded by a 6-mer series of Ser and Gly residues (Gly Ser Gly Ser Ser Gly His His His His His His).

PCR was followed with a DpnI digestion which destroys the methylated template (that doesn't contain the substitution) leaving behind only the unmethylated PCR amplicons with the substitution.

The PCR amplicons are then then directly transformed into chemically competent E. Coli host cells, wherein the bacteria were pre-treated with chemicals to enable them to take up plasmids incorporating the amplicons. See ThermoFisher Scientific, Chemically Competent Cells webpage (featuring kits for generating chemically competent cells).

The mutant T7 DNA ligase polypeptides expressed from the transformed E. Coli host cells were characterized and selected based on a standard ligation assay with gel electrophoresis. Ligase catalyzes the formation of phosphodiester bonds between the 5' and 3' ends of complementary cohesive ends or blunt ends of duplex DNA, and the extent of ligation with different T7 DNA ligase mutants can be visualized on an agarose gel using appropriate DNA dyes. In this case, GelRed (Biotium, San Francisco CA) was used to stain the gels for visualization under UV light. Examining each T7 DNA ligase mutant's performance based on their ligation activity at diminishing concentrations of enzyme, and comparing the resultant activity to that of similarly diluted wild type ("WT") ligase, allowed determination of which mutants showed increased activity compared to the wild-type under the same conditions.

The ligation substrate for characterization of the mutant T7 DNA ligase polypeptides expressed from the transformed E. Coli host cells was prepared as follows.

The DNA vector used was pUC19 (New England Bio Labs, catalog number N3041S). PUC19 is a double stranded circle that is 2686 base pairs long. PUC19 was digested with Bsal-HF®v2 (New England Bio Labs, catalog number R3733S) which has an offset/nonsymmetrical cleavage site, where 5' strand is cleaved after the recognition sequence plus the addition of one random (N1) nucleotide, and on the 3' strand cleavage occurs after the complementary recognition sequence plus five additional random (N5) nucleotides. The 5' recognition sequence is GGTCTC. The cleavage site of pUC19 by Bsal-HF®v2 is designated 5'-GGTCTC (N1)/(N5)-3'.

5 μl of pUC19 at a concentration of 1 mg/ml was combined with 2.5 μl of 20,000 units/ml Bsal-HF®v2, 5 μl 10× rCutSmart™ Buffer (New England Bio Labs, catalog number B6004S) (50 mM Potassium Acetate, 20 mM Tris-acetate, 10 mM Magnesium Acetate, 100 μg/ml Recombinant Albumin), and 35 μl of water. After all components were combined, the composition was incubated at 37° C. for the digestion to take place. After one hour at 37° C., the reaction was incubated at 80° C. for 20 minutes to heat inactivate the Bsal-HF®v2. The mixture was then diluted with water to a concentration of 10 ng/μl.

Example: Ligation Assay and Results

The ligation procedure was performed as follows. Each T7 DNA ligase either wild-type or variant was diluted with enzyme diluent (50% glycerol, 10 mM tris-HCl) in a serial dilution such that for each sample 10 different concentrations were obtained. The starting concentration for each serial dilution was 100 ng/μl T7 DNA ligase, diluted two fold in the next dilution such that the final concentration was 50% as concentrated as the sample before it, and so on for a total of 10 1:2 dilutions. Two μl of each enzyme or serial dilution was then added to a PCR plate such that the approximate amount of the enzyme in lanes 1 to lane 12 is, respectively, 100, 50, 25, 12.5, 6.25, 3.1, 1.5, 0.7, 0.39, 0.2, 0.1, and 0.05 ng.

To the 2 μl enzyme, 13 μl master mix consisting of 4 μl of 5×NEBNext Quick Ligation Reaction Buffer (New England Biolabs, catalog number B6058S; 1× components yield 66 mM Tris-HCl, 10 mM MgCl₂, 1 mM ATP, 10 mM DTT [dithiothreitol], 7.5% Polyethylene glycol [PEG 6000], pH7.6), 0.5 μl of 10 ng/μl pUC19 digested with Bsal-HF®v2, and 13.5 μl of water was added to each reaction for a total reaction volume of 20 μl. The reactions were incubated at 16° C. for 20 minutes. 4 μl of stop solution (120 mM EDTA, 30% glycerol, 50 mM Tris-HCl pH 8.0, 0.0125% bromophenol blue, 0.1% SDS, and 5× Gel Red Nucleic Acid Stain (Biotium, Fremont, CA)) was then added to each reaction.

Gel electrophoresis with 0.8% agarose gel was used to visualize the ligation reaction product. Each gel had a wild-type T7 DNA ligase sample series and 12 variant T7 DNA ligase sample series. Each gel was run for 25 minutes at 200V.

Results as compared with wild type are shown in FIG. 1, a composite image of the gel images for T7 DNA WT and the 13 variants which meet the criteria for increased activity on the cohesive-ended dsDNA substrate. The mutants identified that exhibit increased ligation activity are the following: E63K, K73E, K137E, K174E, E182K, K210E, E243K, D245R, E268K, E272K, E289K, K295E, and D336R.

Comparative activity results are tabulated in Table 1 below, showing the increase in variant activity compared to the WT as calculated using lane differences for each T7 DNA ligase mutant, where each lane difference greater than WT is assigned a 2-fold activity increase. For example, 1 lane activity improvement over WT was given the value 2 (as shown by little or no apparent upper band representing supercoiled plasmid product and little or no apparent middle band representing restriction digested linearized substrate plasmid in a lane), while 2 lanes activity improvement over WT was given the value 4 and so on.

TABLE 1

T7 DNA Ligase variants with greater activity than WT

| Mutants | Activity vs. WT (Fold) |
| --- | --- |
| E63K | 2 |
| K73E | 2 |
| K146E | 8 |
| E174K | 2 |
| E182K | 2 |
| K210E | 2 |
| E243K | 8 |
| D245R | 4 |
| E268K | 2 |
| E272K | 16 |
| E289K | 2 |
| K295E | 4 |
| D336R | 2 |

Using the Mutant T7 DNA Ligases

In certain embodiments, the T7 mutant ligases are used in sequencing methods, including in attaching adapters to library fragments for subsequent sequencing. For example, in some embodiments, the mutant T7 DNA ligases finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in *Genomics,* 92:255 (2008), herein incorporated by reference in its entirety.

Any number of DNA sequencing techniques are suitable, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the mutant T7 DNA ligases find uses in automated sequencing techniques understood in that art. In some embodiments, the mutant T7 DNA ligase finds use in parallel sequencing of partitioned amplicons (PCT Publication No: WO2006084132, herein incorporated by reference in its entirety). In some embodiments, the mutant T7 DNA ligase finds use in DNA sequencing by parallel oligonucleotide extension (See, e.g., U.S. Pat. Nos. 5,750,341, and 6,306,597, both of which are herein incorporated by reference). Additional examples of sequencing techniques in which the mutant T7 DNA ligase use include the Church polony technology (Mitra et al., 2003, Analytical Biochemistry 320, 55-65; Shendure et al., 2005 Science 309, 1728-1732; U.S. Pat. Nos. 6,432,360, 6,485, 944, 6,511,803; all of which are herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; all of which are herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.,* 55:641-658, 2009; MacLean et al., *Nature Rev. Microbiol.,* 7:287-296; each herein incorporated by reference in their entirety). NGS methods can be broadly divided into those that typically use template amplification and those that do not.

Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLID) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., *Clinical Chem.,* 55:641-658, 2009; MacLean et al., *Nature Rev. Microbiol.,* 7:287-296; U.S. Pat. Nos. 6,210,891; 6,258,568; each herein incorporated by reference in its entirety), template DNA is fragmented, end-repaired, ligated to adapters, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and 106 sequence reads can be achieved, resulting in up to 500 million base pairs (Mb) of sequence.

In the Solexa/Illumina platform (Voelkerding et al., *Clinical Chem.*, 55:641-658, 2009; MacLean et al., *Nature Rev. Microbiol.*, 7:287-296; U.S. Pat. Nos. 6,833,246; 7,115,400; 6,969,488; each herein incorporated by reference), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLID technology (Voelkerding et al., *Clinical Chem.*, 55:641-658, 2009; MacLean et al., *Nature Rev. Microbiol.*, 7:287-296; U.S. Pat. Nos. 5,912,148; 6,130,073; each herein incorporated by reference) also involves fragmentation of the template, ligation to oligonucleotide adapters, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLID system, interrogation probes have 16 possible combinations of the two bases at the 3' end of each probe, and one of four fluors at the 5' end. Fluor color, and thus identity of each probe, corresponds to specific color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology descried herein finds use in nanopore sequencing (see, e.g., Astier et al., J. Am. Chem. Soc. 2006 Feb. 8; 128 (5): 1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the mutant T7 DNA ligase finds use in HeliScope by Helicos BioSciences (Voelkerding et al., *Clinical Chem.*, 55:641-658, 2009; MacLean et al., *Nature Rev. Microbiol.*, 7:287-296; U.S. Pat. Nos. 7,169, 560; 7,282,337; 7,482,120; 7,501,245; 6,818,395; 6,911, 345; 7,501,245; each herein incorporated by reference). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics is used. The per-base accuracy of the Ion Torrent sequencer is ~99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

The mutant T7 DNA ligase finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, which is incorporated by reference.

Other single molecule sequencing methods include real-time sequencing by synthesis using a VisiGen platform (Volkerding et al., *Clinical Chem.*, 55:641-58, 2009; U.S. Pat. No. 7,329,492; U.S. patent application Ser. No. 11/671, 956; U.S. patent application Ser. No. 11/781,166; each herein incorporated by reference) in which immobilized, primed DNA template is subjected to strand extension using a fluorescently-modified polymerase and florescent acceptor molecules, resulting in detectible fluorescence resonance energy transfer (FRET) upon nucleotide addition.

The specific methods and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, including but not limited to Variant Sequences, and that such modifications and variations are within the scope of this invention as defined by the appended claims.

Pertinent Sequences

```
DNA sequence of T7 DNA Ligase Wild Type
                                                          SEQ ID NO: 1
 001  ATGAATATCAAGACTAATCCGTTTAAAGCAGTATCGTTCGTGGAAAGCGCGATCAAAAAA     060

061  GCCTTGGACAACGCTGGTTATTTAATCGCAGAAATTAAATATGATGGTGTCAGAGGGAAC     120

121  ATCTGCGTCGATAATACGGCCAATTCGTATTGGCTGAGCCGTGTGTCTAAAACTATTCCG     180

181  GCACTCGAACACCTGAATGGTTTTGATGTTAGATGGAAACGCCTTTTAAATGACGATCGG     240

241  TGTTTTTACAAAGATGGCTTTATGCTGGATGGGGAACTGATGGTTAAAGGCGTCGATTTC     300

301  AATACCGGATCTGGGTTATTACGTACGAAATGGACTGACACAAAAAATCAAGAATTTCAC     360

361  GAAGAATTATTTGTAGAACCAATTCGAAAAAAGGATAAAGTGCCTTTTAAGTTACATACA     420

421  GGCCATCTGCATATAAAGCTCTATGCGATACTGCCCCTTCACATTGTGGAAAGCGGTGAG     480

481  GATTGTGACGTCATGACGCTGCTGATGCAGGAACATGTGAAAAACATGTTACCTCTGTTA     540

541  CAAGAATATTTTCCAGAGATTGAGTGGCAGGCCGCGGAATCCTATGAAGTTTATGACATG     600

601  GTAGAACTCCAGCAGTTGTATGAACAAAAACGCGCCGAAGGGCACGAAGGATTGATCGTC     660

661  AAAGATCCCATGTGTATCTATAAACGGGGTAAAAAATCCGGTTGGTGGAAAATGAAACCG     720

721  GAAAACGAAGCGGATGGTATAATTCAGGGACTGGTGTGGGGTACGAAAGGATTAGCGAAT     780

781  GAAGGCAAAGTCATCGGTTTTGAAGTTTTGCTGGAAAGCGGTCGCCTCGTCAATGCGACA     840

841  AACATCAGTCGGGCACTGATGGATGAGTTCACAGAGACCGTGAAAGAAGCGACCTTGTCT     900

901  CAGTGGGGCTTCTTTTCTCCTTACGGTATAGGAGATAATGATGCTTGTACTATTAATCCG     960

961  TATGACGGATGGGCATGTCAGATCAGTTACATGGAAGAAACTCCTGACGGTTCACTGCGC     1020

1021  CATCCCAGCTTCGTGATGTTCCGGGGTACTGAAGATAATCCCCAAGAGAAAATGTAA     1077
```

-continued

Amino acids sequence of T7 DNA Ligase Wild Type

SEQ ID NO: 2
```
001 MNIKTNPFKAVSFVESAIKKALDNAGYLIAEIKYDGVRGNICVDNTANSYWLSRVSKTIP    060

061 ALEHLNGFDVRWKRLLNDDRCFYKDGFMLDGELMVKGVDFNTGSGLLRTKWTDTKNQEFH    120

121 EELFVEPIRKKDKVPFKLHTGHLHIKLYAILPLHIVESGEDCDVMTLLMQEHVKNMLPLL    180

181 QEYFPEIEWQAAESYEVYDMVELQQLYEQKRAEGHEGLIVKDPMCIYKRGKKSGWWKMKP    240

241 ENEADGIIQGLVWGTKGLANEGKVIGFEVLLESGRLVNATNISRALMDEFTETVKEATLS    300

301 QWGFFSPYGIGDNDACTINPYDGWACQISYMEETPDGSLRHPSFVMFRGTEDNPQEKM    358
```

DNA sequence of T7 DNA Ligase E63K

SEQ ID NO: 3
```
001 ATGAATATCAAGACTAATCCGTTTAAAGCAGTATCGTTCGTGGAAAGCGCGATCAAAAAA    060

061 GCCTTGGACAACGCTGGTTATTTAATCGCAGAAATTAAATATGATGGTGTCAGAGGGAAC    120

121 ATCTGCGTCGATAATACGGCCAATTCGTATTGGCTGAGCCGTGTGTCTAAAACTATTCCG    180

181 GCACTCAAACACCTGAATGGTTTTGATGTTAGATGGAAACGCCTTTTAAATGACGATCGG    240

241 TGTTTTTACAAAGATGGCTTTATGCTGGATGGGGAACTGATGGTTAAAGGCGTCGATTTC    300

301 AATACCGGATCTGGGTTATTACGTACGAAATGGACTGACACAAAAAATCAAGAATTTCAC    360

361 GAAGAATTATTTGTAGAACCAATTCGAAAAAAGGATAAAGTGCCTTTTAAGTTACATACA    420

421 GGCCATCTGCATATAAAGCTCTATGCGATACTGCCCCTTCACATTGTGGAAAGCGGTGAG    480

481 GATTGTGACGTCATGACGCTGCTGATGCAGGAACATGTGAAAAACATGTTACCTCTGTTA    540

541 CAAGAATATTTTCCAGAGATTGAGTGGCAGGCCGCGGAATCCTATGAAGTTTATGACATG    600

601 GTAGAACTCCAGCAGTTGTATGAACAAAAACGCGCCGAAGGGCACGAAGGATTGATCGTC    660

661 AAAGATCCCATGTGTATCTATAAACGGGGTAAAAAATCCGGTTGGTGGAAAATGAAACCG    720

721 GAAAACGAAGCGGATGGTATAATTCAGGGACTGGTGTGGGGTACGAAAGGATTAGCGAAT    780

781 GAAGGCAAAGTCATCGGTTTTGAAGTTTTGCTGGAAAGCGGTCGCCTCGTCAATGCGACA    840

841 AACATCAGTCGGGCACTGATGGATGAGTTCACAGAGACCGTGAAAGAAGCGACCTTGTCT    900

901 CAGTGGGGCTTCTTTTCTCCTTACGGTATAGGAGATAATGATGCTTGTACTATTAATCCG    960

961 TATGACGGATGGGCATGTCAGATCAGTTACATGGAAGAAACTCCTGACGGTTCACTGCGC    1020

1021 CATCCCAGCTTCGTGATGTTCCGGGGTACTGAAGATAATCCCCAAGAGAAAATGTAA    1077
```

Amino acid sequence of T7 DNA Ligase E63K

SEQ ID NO: 4
```
001 MNIKTNPFKAVSFVESAIKKALDNAGYLIAEIKYDGVRGNICVDNTANSYWLSRVSKTIP    060

061 ALKHLNGFDVRWKRLLNDDRCFYKDGFMLDGELMVKGVDFNTGSGLLRTKWTDTKNQEFH    120

121 EELFVEPIRKKDKVPFKLHTGHLHIKLYAILPLHIVESGEDCDVMTLLMQEHVKNMLPLL    180

181 QEYFPEIEWQAAESYEVYDMVELQQLYEQKRAEGHEGLIVKDPMCIYKRGKKSGWWKMKP    240

241 ENEADGIIQGLVWGTKGLANEGKVIGFEVLLESGRLVNATNISRALMDEFTETVKEATLS    300

301 QWGFFSPYGIGDNDACTINPYDGWACQISYMEETPDGSLRHPSFVMFRGTEDNPQEKM    358
```

DNA sequence of T7 DNA Ligase K73E

SEQ ID NO: 5
```
001 ATGAATATCAAGACTAATCCGTTTAAAGCAGTATCGTTCGTGGAAAGCGCGATCAAAAAA    060

061 GCCTTGGACAACGCTGGTTATTTAATCGCAGAAATTAAATATGATGGTGTCAGAGGGAAC    120

121 ATCTGCGTCGATAATACGGCCAATTCGTATTGGCTGAGCCGTGTGTCTAAAACTATTCCG    180

181 GCACTCGAACACCTGAATGGTTTTGATGTTAGATGGGAACGCCTTTTAAATGACGATCGG    240

241 TGTTTTTACAAAGATGGCTTTATGCTGGATGGGGAACTGATGGTTAAAGGCGTCGATTTC    300

301 AATACCGGATCTGGGTTATTACGTACGAAATGGACTGACACAAAAAATCAAGAATTTCAC    360

361 GAAGAATTATTTGTAGAACCAATTCGAAAAAAGGATAAAGTGCCTTTTAAGTTACATACA    420
```

-continued

```
421 GGCCATCTGCATATAAAGCTCTATGCGATACTGCCCCTTCACATTGTGGAAAGCGGTGAG    480

481 GATTGTGACGTCATGACGCTGCTGATGCAGGAACATGTGAAAAACATGTTACCTCTGTTA    540

541 CAAGAATATTTTCCAGAGATTGAGTGGCAGGCCGCGGAATCCTATGAAGTTTATGACATG    600

601 GTAGAACTCCAGCAGTTGTATGAACAAAAACGCGCCGAAGGGCACGAAGGATTGATCGTC    660

661 AAAGATCCCATGTGTATCTATAAACGGGGTAAAAAATCCGGTTGGTGGAAAATGAAACCG    720

721 GAAAACGAAGCGGATGGTATAATTCAGGGACTGGTGTGGGGTACGAAAGGATTAGCGAAT    780

781 GAAGGCAAAGTCATCGGTTTTGAAGTTTTGCTGGAAAGCGGTCGCCTCGTCAATGCGACA    840

841 AACATCAGTCGGGCACTGATGGATGAGTTCACAGAGACCGTGAAAGAAGCGACCTTGTCT    900

901 CAGTGGGGCTTCTTTTCTCCTTACGGTATAGGAGATAATGATGCTTGTACTATTAATCCG    960

961 TATGACGGATGGGCATGTCAGATCAGTTACATGGAAGAAACTCCTGACGGTTCACTGCGC    1020

1021 CATCCCAGCTTCGTGATGTTCCGGGGTACTGAAGATAATCCCCAAGAGAAATGTAA    1077
```

Amino acids sequence of T7 DNA Ligase K73E

```
                                                             SEQ ID NO: 6
001 MNIKTNPFKAVSFVESAIKKALDNAGYLIAEIKYDGVRGNICVDNTANSYWLSRVSKTIP    060

061 ALEHLNGFDVRWERLLNDDRCFYKDGFMLDGELMVKGVDFNTGSGLLRTKWTDTKNQEFH    120
              ‾
121 EELFVEPIRKKDKVPFKLHTGHLHIKLYAILPLHIVESGEDCDVMTLLMQEHVKNMLPLL    180

181 QEYFPEIEWQAAESYEVYDMVELQQLYEQKRAEGHEGLIVKDPMCIYKRGKKSGWWKMKP    240

241 ENEADGIIQGLVWGTKGLANEGKVIGFEVLLESGRLVNATNISRALMDEFTETVKEATLS    300

301 QWGFFSPYGIGDNDACTINPYDGWACQISYMEETPDGSLRHPSFVMFRGTEDNPQEKM    358
```

Amino acid sequence of T7 DNA Ligase K137E

```
                                                             SEQ ID NO: 7
001 MNIKTNPFKAVSFVESAIKKALDNAGYLIAEIKYDGVRGNICVDNTANSYWLSRVSKTIP    060

061 ALKHLNGFDVRWKRLLNDDRCFYKDGFMLDGELMVKGVDFNTGSGLLRTKWTDTKNQEFH    120

121 EELFVEPIRKKDKVPFELHTGHLHIKLYAILPLHIVESGEDCDVMTLLMQEHVKNMLPLL    180
                  ‾
181 QEYFPEIEWQAAESYEVYDMVELQQLYEQKRAEGHEGLIVKDPMCIYKRGKKSGWWKMKP    240

241 ENEADGIIQGLVWGTKGLANEGKVIGFEVLLESGRLVNATNISRALMDEFTETVKEATLS    300

301 QWGFFSPYGIGDNDACTINPYDGWACQISYMEETPDGSLRHPSFVMFRGTEDNPQEKM    358
```

DNA sequence of T7 DNA Ligase K174E

```
                                                             SEQ ID NO: 8
```

```
001 ATGAATATCAAGACTAATCCGTTTAAAGCAGTATCGTTCGTGGAAAGCGCGATCAAAAAA    060

061 GCCTTGGACAACGCTGGTTATTTAATCGCAGAAATTAAATATGATGGTGTCAGAGGGAAC    120

121 ATCTGCGTCGATAATACGGCCAATTCGTATTGGCTGAGCCGTGTGTCTAAAACTATTCCG    180

181 GCACTCGAACACCTGAATGGTTTTGATGTTAGATGGAAACGCCTTTTAAATGACGATCGG    240

241 TGTTTTTACAAAGATGGCTTTATGCTGGATGGGGAACTGATGGTTAAAGGCGTCGATTTC    300

301 AATACCGGATCTGGGTTATTACGTACGAAATGGACTGACACAAAAAATCAAGAATTTCAC    360

361 GAAGAATTATTTGTAGAACCAATTCGAAAAAAGGATAAAGTGCCTTTTAAGTTACATACA    420

421 GGCCATCTGCATATAAAGCTCTATGCGATACTGCCCCTTCACATTGTGGAAAGCGGTGAG    480

481 GATTGTGACGTCATGACGCTGCTGATGCAGGAACATGTGAGAAACATGTTACCTCTGTTA    540
                                              ‾‾‾
541 CAAGAATATTTTCCAGAGATTGAGTGGCAGGCCGCGGAATCCTATGAAGTTTATGACATG    600

601 GTAGAACTCCAGCAGTTGTATGAACAAAAACGCGCCGAAGGGCACGAAGGATTGATCGTC    660

661 AAAGATCCCATGTGTATCTATAAACGGGGTAAAAAATCCGGTTGGTGGAAAATGAAACCG    720

721 GAAAACGAAGCGGATGGTATAATTCAGGGACTGGTGTGGGGTACGAAAGGATTAGCGAAT    780
```

-continued

```
781 GAAGGCAAAGTCATCGGTTTTGAAGTTTTGCTGGAAAGCGGTCGCCTCGTCAATGCGACA        840

841 AACATCAGTCGGGCACTGATGGATGAGTTCACAGAGACCGTGAAAGAAGCGACCTTGTCT        900

901 CAGTGGGGCTTCTTTTCTCCTTACGGTATAGGAGATAATGATGCTTGTACTATTAATCCG        960

961 TATGACGGATGGGCATGTCAGATCAGTTACATGGAAGAAACTCCTGACGGTTCACTGCGC       1020

1021 CATCCCAGCTTCGTGATGTTCCGGGGTACTGAAGATAATCCCCAAGAGAAAATGTAA        1077
```

Amino acid sequence of T7 DNA Ligase K174E

SEQ ID NO: 9
```
001 MNIKTNPFKAVSFVESAIKKALDNAGYLIAEIKYDGVRGNICVDNTANSYWLSRVSKTIP        060

061 ALEHLNGFDVRWKRLLNDDRCFYKDGFMLDGELMVKGVDFNTGSGLLRTKWTDTKNQEFH        120

121 EELFVEPIRKKDKVPFKLHTGHLHIKLYAILPLHIVESGEDCDVMTLLMQEHVENMLPLL        180

181 QEYFPEIEWQAAESYEVYDMVELQQLYEQKRAEGHEGLIVKDPMCIYKRGKKSGWWKMKP        240

241 ENEADGIIQGLVWGTKGLANEGKVIGFEVLLESGRLVNATNISRALMDEFTETVKEATLS        300

301 QWGFFSPYGIGDNDACTINPYDGWACQISYMEETPDGSLRHPSFVMFRGTEDNPQEKM        358
```

DNA sequence of T7 DNA Ligase E182K

SEQ ID NO: 10
```
001 ATGAATATCAAGACTAATCCGTTTAAAGCAGTATCGTTCGTGGAAAGCGCGATCAAAAAA        060

061 GCCTTGGACAACGCTGGTTATTTAATCGCAGAAATTAAATATGATGGTGTCAGAGGGAAC        120

121 ATCTGCGTCGATAATACGGCCAATTCGTATTGGCTGAGCCGTGTGTCTAAAACTATTCCG        180

181 GCACTCGAACACCTGAATGGTTTTGATGTTAGATGGAAACGCCTTTTAAATGACGATCGG        240

241 TGTTTTTACAAAGATGGCTTTATGCTGGATGGGGAACTGATGGTTAAAGGCGTCGATTTC        300

301 AATACCGGATCTGGGTTATTACGTACGAAATGGACTGACACAAAAAATCAAGAATTTCAC        360

361 GAAGAATTATTTGTAGAACCAATTCGAAAAAAGGATAAAGTGCCTTTTAAGTTACATACA        420

421 GGCCATCTGCATATAAAGCTCTATGCGATACTGCCCCTTCACATTGTGGAAAGCGGTGAG        480

481 GATTGTGACGTCATGACGCTGCTGATGCAGGAACATGTGAAAAACATGTTACCTCTGTTA        540

541 CAAAAATATTTTCCAGAGATTGAGTGGCAGGCCGCGGAATCCTATGAAGTTTATGACATG        600

601 GTAGAACTCCAGCAGTTGTATGAACAAAAACGCGCCGAAGGGCACGAAGGATTGATCGTC        660

661 AAAGATCCCATGTGTATCTATAAACGGGGTAAAAAATCCGGTTGGTGGAAAATGAAACCG        720

721 GAAAACGAAGCGGATGGTATAATTCAGGGACTGGTGTGGGGTACGAAAGGATTAGCGAAT        780

781 GAAGGCAAAGTCATCGGTTTTGAAGTTTTGCTGGAAAGCGGTCGCCTCGTCAATGCGACA        840

841 AACATCAGTCGGGCACTGATGGATGAGTTCACAGAGACCGTGAAAGAAGCGACCTTGTCT        900

901 CAGTGGGGCTTCTTTTCTCCTTACGGTATAGGAGATAATGATGCTTGTACTATTAATCCG        960

961 TATGACGGATGGGCATGTCAGATCAGTTACATGGAAGAAACTCCTGACGGTTCACTGCGC       1020

1021 CATCCCAGCTTCGTGATGTTCCGGGGTACTGAAGATAATCCCCAAGAGAAAATGTAA        1077
```

Amino acid sequence of T7 DNA Ligase E182K

SEQ ID NO: 11
```
001 MNIKTNPFKAVSFVESAIKKALDNAGYLIAEIKYDGVRGNICVDNTANSYWLSRVSKTIP        060

061 ALEHLNGFDVRWKRLLNDDRCFYKDGFMLDGELMVKGVDFNTGSGLLRTKWTDTKNQEFH        120

121 EELFVEPIRKKDKVPFKLHTGHLHIKLYAILPLHIVESGEDCDVMTLLMQEHVKNMLPLL        180

181 QKYFPEIEWQAAESYEVYDMVELQQLYEQKRAEGHEGLIVKDPMCIYKRGKKSGWWKMKP        240

241 ENEADGIIQGLVWGTKGLANEGKVIGFEVLLESGRLVNATNISRALMDEFTETVKEATLS        300

301 QWGFFSPYGIGDNDACTINPYDGWACQISYMEETPDGSLRHPSFVMFRGTEDNPQEKM        358
```

-continued

DNA sequence of T7 DNA Ligase K210E

SEQ ID NO: 12

```
001 ATGAATATCAAGACTAATCCGTTTAAAGCAGTATCGTTCGTGGAAAGCGCGATCAAAAAA   060

061 GCCTTGGACAACGCTGGTTATTTAATCGCAGAAATTAAATATGATGGTGTCAGAGGGAAC   120

121 ATCTGCGTCGATAATACGGCCAATTCGTATTGGCTGAGCCGTGTGTCTAAAACTATTCCG   180

181 GCACTCGAACACCTGAATGGTTTTGATGTTAGATGGAAACGCCTTTTAAATGACGATCGG   240

241 TGTTTTTACAAAGATGGCTTTATGCTGGATGGGGAACTGATGGTTAAAGGCGTCGATTTC   300

301 AATACCGGATCTGGGTTATTACGTACGAAATGGACTGACACAAAAAATCAAGAATTTCAC   360

361 GAAGAATTATTTGTAGAACCAATTCGAAAAAAGGATAAAGTGCCTTTTAAGTTACATACA   420

421 GGCCATCTGCATATAAAGCTCTATGCGATACTGCCCCTTCACATTGTGGAAAGCGGTGAG   480

481 GATTGTGACGTCATGACGCTGCTGATGCAGGAACATGTGAAAAACATGTTACCTCTGTTA   540

541 CAAGAATATTTTCCAGAGATTGAGTGGCAGGCCGCGGAATCCTATGAAGTTTATGACATG   600

601 GTAGAACTCCAGCAGTTGTATGAACAGAAACGCGCCGAAGGGCACGAAGGATTGATCGTC   660

661 AAAGATCCCATGTGTATCTATAAACGGGGTAAAAAATCCGGTTGGTGGAAAATGAAACCG   720

721 GAAAACGAAGCGGATGGTATAATTCAGGGACTGGTGTGGGGTACGAAAGGATTAGCGAAT   780

781 GAAGGCAAAGTCATCGGTTTTGAAGTTTTGCTGGAAAGCGGTCGCCTCGTCAATGCGACA   840

841 AACATCAGTCGGGCACTGATGGATGAGTTCACAGAGACCGTGAAAGAAGCGACCTTGTCT   900

901 CAGTGGGGCTTCTTTTCTCCTTACGGTATAGGAGATAATGATGCTTGTACTATTAATCCG   960

961 TATGACGGATGGGCATGTCAGATCAGTTACATGGAAGAAACTCCTGACGGTTCACTGCGC   1020

1021 CATCCCAGCTTCGTGATGTTCCGGGGTACTGAAGATAATCCCCAAGAGAAATGTAA   1077
```

Amino acid sequence of T7 DNA Ligase K210E

SEQ ID NO: 13

```
001 MNIKTNPFKAVSFVESAIKKALDNAGYLIAEIKYDGVRGNICVDNTANSYWLSRVSKTIP   060

061 ALEHLNGFDVRWKRLLNDDRCFYKDGFMLDGELMVKGVDFNTGSGLLRTKWTDTKNQEFH   120

121 EELFVEPIRKKDKVPFKLHTGHLHIKLYAILPLHIVESGEDCDVMTLLMQEHVKNMLPLL   180

181 QEYFPEIEWQAAESYEVYDMVELQQLYEQRAEGHEGLIVKDPMCIYKRGKKSGWWKMKP   240

241 ENEADGIIQGLVWGTKGLANEGKVIGFEVLLESGRLVNATNISRALMDEFTETVKEATLS   300

301 QWGFFSPYGIGDNDACTINPYDGWACQISYMEETPDGSLRHPSFVMFRGTEDNPQEKM   358
```

DNA sequence of T7 DNA Ligase E243K

SEQ ID NO: 14

```
001 ATGAATATCAAGACTAATCCGTTTAAAGCAGTATCGTTCGTGGAAAGCGCGATCAAAAAA   060

061 GCCTTGGACAACGCTGGTTATTTAATCGCAGAAATTAAATATGATGGTGTCAGAGGGAAC   120

121 ATCTGCGTCGATAATACGGCCAATTCGTATTGGCTGAGCCGTGTGTCTAAAACTATTCCG   180

181 GCACTCGAACACCTGAATGGTTTTGATGTTAGATGGAAACGCCTTTTAAATGACGATCGG   240

241 TGTTTTTACAAAGATGGCTTTATGCTGGATGGGGAACTGATGGTTAAAGGCGTCGATTTC   300

301 AATACCGGATCTGGGTTATTACGTACGAAATGGACTGACACAAAAAATCAAGAATTTCAC   360

361 GAAGAATTATTTGTAGAACCAATTCGAAAAAAGGATAAAGTGCCTTTTAAGTTACATACA   420

421 GGCCATCTGCATATAAAGCTCTATGCGATACTGCCCCTTCACATTGTGGAAAGCGGTGAG   480

481 GATTGTGACGTCATGACGCTGCTGATGCAGGAACATGTGAAAAACATGTTACCTCTGTTA   540

541 CAAGAATATTTTCCAGAGATTGAGTGGCAGGCCGCGGAATCCTATGAAGTTTATGACATG   600

601 GTAGAACTCCAGCAGTTGTATGAACAAAAACGCGCCGAAGGGCACGAAGGATTGATCGTC   660

661 AAAGATCCCATGTGTATCTATAAACGGGGTAAAAAATCCGGTTGGTGGAAAATGAAACCG   720

721 GAAAACAAAGCGGATGGTATAATTCAGGGACTGGTGTGGGGTACGAAAGGATTAGCGAAT   780

781 GAAGGCAAAGTCATCGGTTTTGAAGTTTTGCTGGAAAGCGGTCGCCTCGTCAATGCGACA   840
```

-continued

```
 841 AACATCAGTCGGGCACTGATGGATGAGTTCACAGAGACCGTGAAAGAAGCGACCTTGTCT        900

901 CAGTGGGGCTTCTTTTCTCCTTACGGTATAGGAGATAATGATGCTTGTACTATTAATCCG        960

961 TATGACGGATGGGCATGTCAGATCAGTTACATGGAAGAAACTCCTGACGGTTCACTGCGC       1020

1021 CATCCCAGCTTCGTGATGTTCCGGGGTACTGAAGATAATCCCCAAGAGAAATGTAA         1077
```

Amino acids sequence of T7 DNA Ligase E243K

SEQ ID NO: 15
```
001 MNIKTNPFKAVSFVESAIKKALDNAGYLIAEIKYDGVRGNICVDNTANSYWLSRVSKTIP        060

061 ALEHLNGFDVRWKRLLNDDRCFYKDGFMLDGELMVKGVDFNTGSGLLRTKWTDTKNQEFH        120

121 EELFVEPIRKKDKVPFKLHTGHLHIKLYAILPLHIVESGEDCDVMTLLMQEHVKNMLPLL        180

181 QEYFPEIEWQAAESYEVYDMVELQQLYEQKRAEGHEGLIVKDPMCIYKRGKKSGWWKMKP        240

241 ENKADGIIQGLVWGTKGLANEGKVIGFEVLLESGRLVNATNISRALMDEFTETVKEATLS        300
        _
301 QWGFFSPYGIGDNDACTINPYDGWACQISYMEETPDGSLRHPSFVMFRGTEDNPQEKM         358
```

DNA sequence of T7 DNA Ligase D245R

SEQ ID NO: 16
```
001 ATGAATATCAAGACTAATCCGTTTAAAGCAGTATCGTTCGTGGAAAGCGCGATCAAAAAA        060

061 GCCTTGGACAACGCTGGTTATTTAATCGCAGAAATTAAATATGATGGTGTCAGAGGGAAC        120

121 ATCTGCGTCGATAATACGGCCAATTCGTATTGGCTGAGCCGTGTGTCTAAAACTATTCCG        180

181 GCACTCGAACACCTGAATGGTTTTGATGTTAGATGGAAACGCCTTTTAAATGACGATCGG        240

241 TGTTTTTACAAAGATGGCTTTATGCTGGATGGGGAACTGATGGTTAAAGGCGTCGATTTC        300

301 AATACCGGATCTGGGTTATTACGTACGAAATGGACTGACACAAAAAATCAAGAATTTCAC        360

361 GAAGAATTATTTGTAGAACCAATTCGAAAAAAGGATAAAGTGCCTTTTAAGTTACATACA        420

421 GGCCATCTGCATATAAAGCTCTATGCGATACTGCCCCTTCACATTGTGGAAAGCGGTGAG        480

481 GATTGTGACGTCATGACGCTGCTGATGCAGGAACATGTGAAAAACATGTTACCTCTGTTA        540

541 CAAGAATATTTTCCAGAGATTGAGTGGCAGGCCGCGAATCCTATGAAGTTTATGACATG        600

601 GTAGAACTCCAGCAGTTGTATGAACAAAAACGCGCCGAAGGGCACGAAGGATTGATCGTC        660

661 AAAGATCCCATGTGTATCTATAAACGGGGTAAAAAATCCGGTTGGTGGAAAATGAAACCG        720

721 GAAAACGAAGCGCGTGGTATAATTCAGGGACTGGTGTGGGGTACGAAAGGATTAGCGAAT        780
                   ___
781 GAAGGCAAAGTCATCGGTTTTGAAGTTTTGCTGGAAAGCGGTCGCCTCGTCAATGCGACA        840

841 AACATCAGTCGGGCACTGATGGATGAGTTCACAGAGACCGTGAAAGAAGCGACCTTGTCT        900

901 CAGTGGGGCTTCTTTTCTCCTTACGGTATAGGAGATAATGATGCTTGTACTATTAATCCG        960

961 TATGACGGATGGGCATGTCAGATCAGTTACATGGAAGAAACTCCTGACGGTTCACTGCGC       1020

1021 CATCCCAGCTTCGTGATGTTCCGGGGTACTGAAGATAATCCCCAAGAGAAATGTAA         1077
```

Amino acids sequence of T7 DNA Ligase D245R

SEQ ID NO: 17
```
001 MNIKTNPFKAVSFVESAIKKALDNAGYLIAEIKYDGVRGNICVDNTANSYWLSRVSKTIP        060

061 ALEHLNGFDVRWKRLLNDDRCFYKDGFMLDGELMVKGVDFNTGSGLLRTKWTDTKNQEFH        120

121 EELFVEPIRKKDKVPFKLHTGHLHIKLYAILPLHIVESGEDCDVMTLLMQEHVKNMLPLL        180

181 QEYFPEIEWQAAESYEVYDMVELQQLYEQKRAEGHEGLIVKDPMCIYKRGKKSGWWKMKP        240

241 ENEARGIIQGLVWGTKGLANEGKVIGFEVLLESGRLVNATNISRALMDEFTETVKEATLS        300
         __
301 QWGFFSPYGIGDNDACTINPYDGWACQISYMEETPDGSLRHPSFVMFRGTEDNPQEKM         358
```

DNA sequence of T7 DNA Ligase E268K

SEQ ID NO: 18
```
001 ATGAATATCAAGACTAATCCGTTTAAAGCAGTATCGTTCGTGGAAAGCGCGATCAAAAAA        060

061 GCCTTGGACAACGCTGGTTATTTAATCGCAGAAATTAAATATGATGGTGTCAGAGGGAAC        120
```

-continued

```
121 ATCTGCGTCGATAATACGGCCAATTCGTATTGGCTGAGCCGTGTGTCTAAAACTATTCCG    180

181 GCACTCGAACACCTGAATGGTTTTGATGTTAGATGGAAACGCCTTTTAAATGACGATCGG    240

241 TGTTTTTACAAAGATGGCTTTATGCTGGATGGGGAACTGATGGTTAAAGGCGTCGATTTC    300

301 AATACCGGATCTGGGTTATTACGTACGAAATGGACTGACACAAAAAATCAAGAATTTCAC    360

361 GAAGAATTATTTGTAGAACCAATTCGAAAAAAGGATAAAGTGCCTTTTAAGTTACATACA    420

421 GGCCATCTGCATATAAAGCTCTATGCGATACTGCCCCTTCACATTGTGGAAAGCGGTGAG    480

481 GATTGTGACGTCATGACGCTGCTGATGCAGGAACATGTGAAAAACATGTTACCTCTGTTA    540

541 CAAGAATATTTTCCAGAGATTGAGTGGCAGGCCGCGGAATCCTATGAAGTTTATGACATG    600

601 GTAGAACTCCAGCAGTTGTATGAACAAAAACGCGCCGAAGGGCACGAAGGATTGATCGTC    660

661 AAAGATCCCATGTGTATCTATAAACGGGGTAAAAAATCCGGTTGGTGGAAAATGAAACCG    720

721 GAAAACGAAGCGGATGGTATAATTCAGGGACTGGTGTGGGGTACGAAAGGATTAGCGAAT    780

781 GAAGGCAAAGTCATCGGTTTT<u>AAA</u>GTTTTGCTGGAAAGCGGTCGCCTCGTCAATGCGACA    840

841 AACATCAGTCGGGCACTGATGGATGAGTTCACAGAGACCGTGAAAGAAGCGACCTTGTCT    900

901 CAGTGGGGCTTCTTTTCTCCTTACGGTATAGGAGATAATGATGCTTGTACTATTAATCCG    960

961 TATGACGGATGGGCATGTCAGATCAGTTACATGGAAGAAACTCCTGACGGTTCACTGCGC   1020

1021 CATCCCAGCTTCGTGATGTTCCGGGGTACTGAAGATAATCCCCAAGAGAAAATGTAA     1077
```

Amino acid sequence of T7 DNA Ligase E268K

SEQ ID NO: 19

```
001 MNIKTNPFKAVSFVESAIKKALDNAGYLIAEIKYDGVRGNICVDNTANSYWLSRVSKTIP    060

061 ALEHLNGFDVRWKRLLNDDRCFYKDGFMLDGELMVKGVDFNTGSGLLRTKWTDTKNQEFH    120

121 EELFVEPIRKKDKVPFKLHTGHLHIKLYAILPLHIVESGEDCDVMTLLMQEHVKNMLPLL    180

181 QEYFPEIEWQAAESYEVYDMVELQQLYEQKRAEGHEGLIVKDPMCIYKRGKKSGWWKMKP    240

241 ENEADGIIQGLVWGTKGLANEGKVIGF<u>K</u>VLLESGRLVNATNISRALMDEFTETVKEATLS    300

301 QWGFFSPYGIGDNDACTINPYDGWACQISYMEETPDGSLRHPSFVMFRGTEDNPQEKM    358
```

DNA sequence of T7 DNA Ligase E272K

SEQ ID NO: 20

```
001 ATGAATATCAAGACTAATCCGTTTAAAGCAGTATCGTTCGTGGAAAGCGCGATCAAAAAA    060

061 GCCTTGGACAACGCTGGTTATTTAATCGCAGAAATTAAATATGATGGTGTCAGAGGGAAC    120

121 ATCTGCGTCGATAATACGGCCAATTCGTATTGGCTGAGCCGTGTGTCTAAAACTATTCCG    180

181 GCACTCGAACACCTGAATGGTTTTGATGTTAGATGGAAACGCCTTTTAAATGACGATCGG    240

241 TGTTTTTACAAAGATGGCTTTATGCTGGATGGGGAACTGATGGTTAAAGGCGTCGATTTC    300

301 AATACCGGATCTGGGTTATTACGTACGAAATGGACTGACACAAAAAATCAAGAATTTCAC    360

361 GAAGAATTATTTGTAGAACCAATTCGAAAAAAGGATAAAGTGCCTTTTAAGTTACATACA    420

421 GGCCATCTGCATATAAAGCTCTATGCGATACTGCCCCTTCACATTGTGGAAAGCGGTGAG    480

481 GATTGTGACGTCATGACGCTGCTGATGCAGGAACATGTGAAAAACATGTTACCTCTGTTA    540

541 CAAGAATATTTTCCAGAGATTGAGTGGCAGGCCGCGGAATCCTATGAAGTTTATGACATG    600

601 GTAGAACTCCAGCAGTTGTATGAACAAAAACGCGCCGAAGGGCACGAAGGATTGATCGTC    660

661 AAAGATCCCATGTGTATCTATAAACGGGGTAAAAAATCCGGTTGGTGGAAAATGAAACCG    720

721 GAAAACGAAGCGGATGGTATAATTCAGGGACTGGTGTGGGGTACGAAAGGATTAGCGAAT    780

781 GAAGGCAAAGTCATCGGTTTTGAAGTTTTGCTG<u>AAA</u>AGCGGTCGCCTCGTCAATGCGACA    840

841 AACATCAGTCGGGCACTGATGGATGAGTTCACAGAGACCGTGAAAGAAGCGACCTTGTCT    900

901 CAGTGGGGCTTCTTTTCTCCTTACGGTATAGGAGATAATGATGCTTGTACTATTAATCCG    960

961 TATGACGGATGGGCATGTCAGATCAGTTACATGGAAGAAACTCCTGACGGTTCACTGCGC   1020
```

-continued

```
1021 CATCCCAGCTTCGTGATGTTCCGGGGTACTGAAGATAATCCCCAAGAGAAAATGTAA      1077
```

Amino acid sequence of T7 DNA Ligase E272K

SEQ ID NO: 21

```
001 MNIKTNPFKAVSFVESAIKKALDNAGYLIAEIKYDGVRGNICVDNTANSYWLSRVSKTIP      060

061 ALEHLNGFDVRWKRLLNDDRCFYKDGFMLDGELMVKGVDFNTGSGLLRTKWTDTKNQEFH      120

121 EELFVEPIRKKDKVPFKLHTGHLHIKLYAILPLHIVESGEDCDVMTLLMQEHVKNMLPLL      180

181 QEYFPEIEWQAAESYEVYDMVELQQLYEQKRAEGHEGLIVKDPMCIYKRGKKSGWWKMKP      240

241 ENEADGIIQGLVWGTKGLANEGKVIGFEVLLKSGRLVNATNISRALMDEFTETVKEATLS      300

301 QWGFFSPYGIGDNDACTINPYDGWACQISYMEETPDGSLRHPSFVMFRGTEDNPQEKM      358
```

DNA sequence of T7 DNA Ligase E289K

SEQ ID NO: 22

```
001 ATGAATATCAAGACTAATCCGTTTAAAGCAGTATCGTTCGTGGAAAGCGCGATCAAAAAA      060

061 GCCTTGGACAACGCTGGTTATTTAATCGCAGAAATTAAATATGATGGTGTCAGAGGGAAC      120

121 ATCTGCGTCGATAATACGGCCAATTCGTATTGGCTGAGCCGTGTGTCTAAAACTATTCCG      180

181 GCACTCGAACACCTGAATGGTTTTGATGTTAGATGGAAACGCCTTTTAAATGACGATCGG      240

241 TGTTTTTACAAAGATGGCTTTATGCTGGATGGGGAACTGATGGTTAAAGGCGTCGATTTC      300

301 AATACCGGATCTGGGTTATTACGTACGAAATGGACTGACACAAAAAATCAAGAATTTCAC      360

361 GAAGAATTATTTGTAGAACCAATTCGAAAAAAGGATAAAGTGCCTTTTAAGTTACATACA      420

421 GGCCATCTGCATATAAAGCTCTATGCGATACTGCCCCTTCACATTGTGGAAAGCGGTGAG      480

481 GATTGTGACGTCATGACGCTGCTGATGCAGGAACATGTGAAAAACATGTTACCTCTGTTA      540

541 CAAGAATATTTTCCAGAGATTGAGTGGCAGGCCGCGGAATCCTATGAAGTTTATGACATG      600

601 GTAGAACTCCAGCAGTTGTATGAACAAAAACGCGCCGAAGGGCACGAAGGATTGATCGTC      660

661 AAAGATCCCATGTGTATCTATAAACGGGGTAAAAAATCCGGTTGGTGGAAAATGAAACCG      720

721 GAAAACGAAGCGGATGGTATAATTCAGGGACTGGTGTGGGGTACGAAAGGATTAGCGAAT      780

781 GAAGGCAAAGTCATCGGTTTTGAAGTTTTGCTGGAAAGCGGTCGCCTCGTCAATGCGACA      840

841 AACATCAGTCGGGCACTGATGGATAAGTTCACAGAGACCGTGAAAGAAGCGACCTTGTCT      900

901 CAGTGGGGCTTCTTTTCTCCTTACGGTATAGGAGATAATGATGCTTGTACTATTAATCCG      960

961 TATGACGGATGGGCATGTCAGATCAGTTACATGGAAGAAACTCCTGACGGTTCACTGCGC      1020

1021 CATCCCAGCTTCGTGATGTTCCGGGGTACTGAAGATAATCCCCAAGAGAAAATGTAA      1077
```

Amino acid sequence of T7 DNA Ligase E289K

SEQ ID NO: 23

```
001 MNIKTNPFKAVSFVESAIKKALDNAGYLIAEIKYDGVRGNICVDNTANSYWLSRVSKTIP      060

061 ALEHLNGFDVRWKRLLNDDRCFYKDGFMLDGELMVKGVDFNTGSGLLRTKWTDTKNQEFH      120

121 EELFVEPIRKKDKVPFKLHTGHLHIKLYAILPLHIVESGEDCDVMTLLMQEHVKNMLPLL      180

181 QEYFPEIEWQAAESYEVYDMVELQQLYEQKRAEGHEGLIVKDPMCIYKRGKKSGWWKMKP      240

241 ENEADGIIQGLVWGTKGLANEGKVIGFEVLLESGRLVNATNISRALMDKFTETVKEATLS      300

301 QWGFFSPYGIGDNDACTINPYDGWACQISYMEETPDGSLRHPSFVMFRGTEDNPQEKM      358
```

DNA sequence of T7 DNA Ligase K295E

SEQ ID NO: 24

```
001 ATGAATATCAAGACTAATCCGTTTAAAGCAGTATCGTTCGTGGAAAGCGCGATCAAAAAA      060

061 GCCTTGGACAACGCTGGTTATTTAATCGCAGAAATTAAATATGATGGTGTCAGAGGGAAC      120

121 ATCTGCGTCGATAATACGGCCAATTCGTATTGGCTGAGCCGTGTGTCTAAAACTATTCCG      180

181 GCACTCGAACACCTGAATGGTTTTGATGTTAGATGGAAACGCCTTTTAAATGACGATCGG      240

241 TGTTTTTACAAAGATGGCTTTATGCTGGATGGGGAACTGATGGTTAAAGGCGTCGATTTC      300
```

```
 301 AATACCGGATCTGGGTTATTACGTACGAAATGGACTGACACAAAAAATCAAGAATTTCAC      360

361 GAAGAATTATTTGTAGAACCAATTCGAAAAAAGGATAAAGTGCCTTTTAAGTTACATACA      420

421 GGCCATCTGCATATAAAGCTCTATGCGATACTGCCCCTTCACATTGTGGAAAGCGGTGAG      480

481 GATTGTGACGTCATGACGCTGCTGATGCAGGAACATGTGAAAAACATGTTACCTCTGTTA      540

541 CAAGAATATTTTCCAGAGATTGAGTGGCAGGCCGCGGAATCCTATGAAGTTTATGACATG      600

601 GTAGAACTCCAGCAGTTGTATGAACAAAAACGCGCCGAAGGGCACGAAGGATTGATCGTC      660

661 AAAGATCCCATGTGTATCTATAAACGGGGTAAAAAATCCGGTTGGTGGAAAATGAAACCG      720

721 GAAAACGAAGCGGATGGTATAATTCAGGGACTGGTGTGGGGTACGAAAGGATTAGCGAAT      780

781 GAAGGCAAAGTCATCGGTTTTGAAGTTTTGCTGGAAAGCGGTCGCCTCGTCAATGCGACA      840

841 AACATCAGTCGGGCACTGATGGATGAGTTCACAGAGACCGTGGAAGAAGCGACCTTGTCT      900
                                                        ‾‾

901 CAGTGGGGCTTCTTTTCTCCTTACGGTATAGGAGATAATGATGCTTGTACTATTAATCCG      960

961 TATGACGGATGGGCATGTCAGATCAGTTACATGGAAGAAACTCCTGACGGTTCACTGCGC     1020

1021 CATCCCAGCTTCGTGATGTTCCGGGGTACTGAAGATAATCCCCAAGAGAAAATGTAA       1077
```

Amino acids sequence of T7 DNA Ligase K295E

SEQ ID NO: 25
```
 001 MNIKTNPFKAVSFVESAIKKALDNAGYLIAEIKYDGVRGNICVDNTANSYWLSRVSKTIP      060

061 ALEHLNGFDVRWKRLLNDDRCFYKDGFMLDGELMVKGVDFNTGSGLLRTKWTDTKNQEFH      120

121 EELFVEPIRKKDKVPFKLHTGHLHIKLYAILPLHIVESGEDCDVMTLLMQEHVKNMLPLL      180

181 QEYFPEIEWQAAESYEVYDMVELQQLYEQKRAEGHEGLIVKDPMCIYKRGKKSGWWKMKP      240

241 ENEADGIIQGLVWGTKGLANEGKVIGFEVLLESGRLVNATNISRALMDEFTETVEKATLS      300
                                                          ‾

301 QWGFFSPYGIGDNDACTINPYDGWACQISYMEETPDGSLRHPSFVMFRGTEDNPQEKM       358
```

DNA sequence of T7 DNA Ligase and D336R

SEQ ID NO: 26
```
 001 ATGAATATCAAGACTAATCCGTTTAAAGCAGTATCGTTCGTGGAAAGCGCGATCAAAAAA      060

061 GCCTTGGACAACGCTGGTTATTTAATCGCAGAAATTAAATATGATGGTGTCAGAGGGAAC      120

121 ATCTGCGTCGATAATACGGCCAATTCGTATTGGCTGAGCCGTGTGTCTAAAACTATTCCG      180

181 GCACTCGAACACCTGAATGGTTTTGATGTTAGATGGAAACGCCTTTTAAATGACGATCGG      240

241 TGTTTTTACAAAGATGGCTTTATGCTGGATGGGGAACTGATGGTTAAAGGCGTCGATTTC      300

301 AATACCGGATCTGGGTTATTACGTACGAAATGGACTGACACAAAAAATCAAGAATTTCAC      360

361 GAAGAATTATTTGTAGAACCAATTCGAAAAAAGGATAAAGTGCCTTTTAAGTTACATACA      420

421 GGCCATCTGCATATAAAGCTCTATGCGATACTGCCCCTTCACATTGTGGAAAGCGGTGAG      480

481 GATTGTGACGTCATGACGCTGCTGATGCAGGAACATGTGAAAAACATGTTACCTCTGTTA      540

541 CAAGAATATTTTCCAGAGATTGAGTGGCAGGCCGCGGAATCCTATGAAGTTTATGACATG      600

601 GTAGAACTCCAGCAGTTGTATGAACAAAAACGCGCCGAAGGGCACGAAGGATTGATCGTC      660

661 AAAGATCCCATGTGTATCTATAAACGGGGTAAAAAATCCGGTTGGTGGAAAATGAAACCG      720

721 GAAAACGAAGCGGATGGTATAATTCAGGGACTGGTGTGGGGTACGAAAGGATTAGCGAAT      780

781 GAAGGCAAAGTCATCGGTTTTGAAGTTTTGCTGGAAAGCGGTCGCCTCGTCAATGCGACA      840

841 AACATCAGTCGGGCACTGATGGATGAGTTCACAGAGACCGTGAAAGAAGCGACCTTGTCT      900

901 CAGTGGGGCTTCTTTTCTCCTTACGGTATAGGAGATAATGATGCTTGTACTATTAATCCG      960

961 TATGACGGATGGGCATGTCAGATCAGTTACATGGAAGAAACTCCTCGTGGTTCACTGCGC     1020
                                                      ‾‾‾

1021 CATCCCAGCTTCGTGATGTTCCGGGGTACTGAAGATAATCCCCAAGAGAAAATGTAA       1077
```

-continued

Amino acids sequence of T7 DNA Ligase D336R

SEQ ID NO: 27

```
001 MNIKTNPFKAVSFVESAIKKALDNAGYLIAEIKYDGVRGNICVDNTANSYWLSRVSKTIP       060

061 ALEHLNGFDVRWKRLLNDDRCFYKDGFMLDGELMVKGVDFNTGSGLLRTKWTDTKNQEFH       120

121 EELFVEPIRKKDKVPFKLHTGHLHIKLYAILPLHIVESGEDCDVMTLLMQEHVKNMLPLL       180

181 QEYFPEIEWQAAESYEVYDMVELQQLYEQKRAEGHEGLIVKDPMCIYKRGKKSGWWKMKP       240

241 ENEADGIIQGLVWGTKGLANEGKVIGFEVLLESGRLVNATNISRALMDEFTETVKEATLS       300

301 QWGFFSPYGIGDNDACTINPYDGWACQISYMEETPRGSLRHPSFVMFRGTEDNPQEKM        358
```

---

What is claimed is:

1. A mutant T7 DNA ligase or a biologically active fragment thereof, comprising the mutation E63K (SEQ ID NO:4), but wherein amino acids in SEQ ID NO:4 other than 63K can have a conservative mutation, but only to the extent that there remains at least 90% sequence identity to SEQ ID NO:4.

2. A mutant T7 DNA ligase or a biologically active fragment thereof, comprising the mutation E63K (SEQ ID NO:4), but wherein amino acids in SEQ ID NO:4 other than 63K can have a conservative mutation, but only to the extent that there remains at least 95% sequence identity to SEQ ID NO:4.

3. A mutant T7 DNA ligase of claim 2 wherein amino acids in SEQ ID NO:4 other than 63K can have a conservative mutation, but only to the extent that there remains at least 99% sequence identity to SEQ ID NO:4.

4. A mutant T7 DNA ligase having the amino acid sequence of SEQ ID NO:4.

* * * * *

SEQUENCE LISTING

Sequence total quantity: 27

```
SEQ ID NO: 1             moltype = DNA   length = 1077
FEATURE                  Location/Qualifiers
source                   1..1077
                         mol_type = genomic DNA
                         note = DNA sequence of T7 DNA Ligase Wild Type
                         organism = Teseptimavirus T7
SEQUENCE: 1
atgaatatca agactaatcc gtttaaagca gtatcgttcg tggaaagcgc gatcaaaaaa  60
gccttggaca acgctggtta tttaatcgca gaaattaaat atgatggtgt cagagggaac  120
atctgcgtcg ataatacggc caattcgtat tggctgagcc gtgtgtctaa aactattccg  180
gcactcgaac acctgaatgg ttttgatgtt agatggaaac gcctttttaa tgacgatcgg  240
tgttttttaca aagatggctt tatgctggat ggggaactga tggttaaagg cgtcgatttc  300
aataccggat ctgggttatt acgtacgaaa tggactgaca caaaaaatca agaatttcac  360
gaagaattat ttgtagaacc aattcgaaaa aaggataaag tgcctttaa gttacataca  420
ggccatctgc atataaagct ctatgcgata ctgcccttc acattgtgga aagcggtgag  480
gattgtgacg tcatgacgct gctgatgcag aacatgtga aaaacatgtt acctctgtta  540
caagaatatt ttccagagat tgagtggcag gccgcggaat cctatgaagt ttatgacatg  600
gtagaactcc agcagttgta tgaacaaaaa cgcgccgaag ggcacgaagg attgatcgtc  660
aaagatccca tgtgtatcta taaacggggt aaaaaatccg gttggtggaa atgaaaccg  720
gaaaacgaag cggatggtat aattcaggga ctggtgtggg gtacgaaagg attagcgaat  780
gaaggcaaag tcatcggttt tgaagttttg ctggaaagcg gtcgcctcgt caatgcgaca  840
aacatcagtc gggcactgat ggatgagttc acagagaccg tgaaagaagc gaccttgtct  900
cagtgggggct tcttttctcc ttacggtata ggagataatg atgcttgtac tattaatccg  960
tatgacggat gggcatgtca gatcagttac atggaagaaa ctcctgacgg ttcactgcgc  1020
catcccagct cgtgatgtt ccggggtact gaagataatc cccaagagaa aatgtaa  1077

SEQ ID NO: 2             moltype = AA   length = 358
FEATURE                  Location/Qualifiers
source                   1..358
                         mol_type = protein
                         note = Amino acids sequence of T7 DNA Ligase Wild Type
                         organism = Teseptimavirus T7
SEQUENCE: 2
MNIKTNPFKA VSFVESAIKK ALDNAGYLIA EIKYDGVRGN ICVDNTANSY WLSRVSKTIP  60
ALEHLNGFDV RWKRLLNDDR CFYKDGFMLD GELMVKGVDF NTGSGLLRTK WTDTKNQEFH  120
EELFVEPIRK KDKVPFKLHT GHLHIKLYAI LPLHIVESGE DCDVMTLLMQ EHVKNMLPLL  180
QEYFPEIEWQ AAESYEVYDM VELQQLYEQK RAEGHEGLIV KDPMCIYKRG KKSGWWKMKP  240
ENEADGIIQG LVWGTKGLAN EGKVIGFEVL LESGRLVNAT NISRALMDEF TETVKEATLS  300
QWGFFSPYGI GDNDACTINP YDGWACQISY MEETPDGSLR HPSFVMFRGT EDNPQEKM    358

SEQ ID NO: 3             moltype = DNA   length = 1077
FEATURE                  Location/Qualifiers
source                   1..1077
                         mol_type = genomic DNA
                         note = DNA sequence of T7 DNA Ligase E63K
                         organism = Teseptimavirus T7
SEQUENCE: 3
atgaatatca agactaatcc gtttaaagca gtatcgttcg tggaaagcgc gatcaaaaaa  60
gccttggaca acgctggtta tttaatcgca gaaattaaat atgatggtgt cagagggaac  120
atctgcgtcg ataatacggc caattcgtat tggctgagcc gtgtgtctaa aactattccg  180
gcactcaaac acctgaatgg ttttgatgtt agatggaaac gcctttttaa tgacgatcgg  240
tgttttttaca aagatggctt tatgctggat ggggaactga tggttaaagg cgtcgatttc  300
aataccggat ctgggttatt acgtacgaaa tggactgaca caaaaaatca agaatttcac  360
gaagaattat ttgtagaacc aattcgaaaa aaggataaag tgcctttaa gttacataca  420
ggccatctgc atataaagct ctatgcgata ctgcccttc acattgtgga aagcggtgag  480
gattgtgacg tcatgacgct gctgatgcag aacatgtga aaaacatgtt acctctgtta  540
caagaatatt ttccagagat tgagtggcag gccgcggaat cctatgaagt ttatgacatg  600
gtagaactcc agcagttgta tgaacaaaaa cgcgccgaag ggcacgaagg attgatcgtc  660
aaagatccca tgtgtatcta taaacggggt aaaaaatccg gttggtggaa atgaaaccg  720
gaaaacgaag cggatggtat aattcaggga ctggtgtggg gtacgaaagg attagcgaat  780
```

```
gaaggcaaag tcatcggttt tgaagttttg ctggaaagcg gtcgcctcgt caatgcgaca   840
aacatcagtc gggcactgat ggatgagttc acagagaccg tgaaagaagc gaccttgtct   900
cagtggggct tctttctcc ttacggtata ggagataatg atgcttgtac tattaatccg    960
tatgacggat gggcatgtca gatcagttac atggaagaaa ctcctgacgg ttcactgcgc  1020
catcccagct tcgtgatgtt ccggggtact gaagataatc cccaagagaa aatgtaa     1077
```

```
SEQ ID NO: 4              moltype = AA  length = 358
FEATURE                   Location/Qualifiers
source                    1..358
                          mol_type = protein
                          organism = Teseptimavirus T7
MOD_RES                   63
                          note = Lysin
SEQUENCE: 4
MNIKTNPFKA VSFVESAIKK ALDNAGYLIA EIKYDGVRGN ICVDNTANSY WLSRVSKTIP   60
ALKHLNGFDV RWKRLLNDDR CFYKDGFMLD GELMVKGVDF NTGSGLLRTK WTDTKNQEFH  120
EELFVEPIRK KDKVPFKLHT GHLHIKLYAI LPLHIVESGE DCDVMTLLMQ EHVKNMLPLL  180
QEYFPEIEWQ AAESYEVYDM VELQQLYEQK RAEGHEGLIV KDPMCIYKRG KKSGWWKMKP  240
ENEADGIIQG LVWGTKGLAN EGKVIGFEVL LESGRLVNAT NISRALMDEF TETVKEATLS  300
QWGFFSPYGI GDNDACTINP YDGWACQISY MEETPDGSLR HPSFVMFRGT EDNPQEKM    358
```

```
SEQ ID NO: 5              moltype = DNA  length = 1077
FEATURE                   Location/Qualifiers
source                    1..1077
                          mol_type = genomic DNA
                          note = DNA sequence of T7 DNA Ligase K73E
                          organism = Teseptimavirus T7
SEQUENCE: 5
atgaatatca agactaatcc gtttaaagca gtatcgttcg tggaaagcgc gatcaaaaaa    60
gccttggaca acgctggtta tttaatcgca gaaattaaat atgatggtgt cagagggaac   120
atctgcgtcg ataatacggc caattcgtat tggctgagcc gtgtgtctaa aactattccg   180
gcactcgaac acctgaatgg ttttgatgtt agatgggaac gcctttttaa atgacgatcgg   240
tgttttttaca aagatggctt tatgctggat ggggaactga tggttaaagg cgtcgatttc   300
aataccggat ctgggttatt acgtacgaaa tggactgaca caaaaaatca agaatttcac   360
gaagaattat ttgtagaacc aattcgaaaa aaggataaag tgcctttaa gttacataca    420
ggccatctgc atataaagct ctatgcgata ctgcccctc acattgtgga aagcggtgag   480
gattgtgacg tcatgacgct gctgatgcag gaacatgtga aaaacatgtt acctctgtta   540
caagaatatt ttccagagat tgagtggcag gccgcgaat cctatgaagt ttatgacatg   600
gtagaactcc agcagttgta tgaacaaaaa cgcgccgaag ggcacgaagg attgatcgtc   660
aaagatccca tgtgtatcta taaacgggg aaaaaatccg gttggtggaa aatgaaaccg   720
gaaaacgaag cggatggtat aattcaggga ctggtgtggg gtacgaaagg attagcgaat   780
gaaggcaaag tcatcggttt tgaagttttg ctggaaagcg gtcgcctcgt caatgcgaca   840
aacatcagtc gggcactgat ggatgagttc acagagaccg tgaaagaagc gaccttgtct   900
cagtggggct tctttctcc ttacggtata ggagataatg atgcttgtac tattaatccg    960
tatgacggat gggcatgtca gatcagttac atggaagaaa ctcctgacgg ttcactgcgc  1020
catcccagct tcgtgatgtt ccggggtact gaagataatc cccaagagaa aatgtaa     1077
```

```
SEQ ID NO: 6              moltype = AA  length = 358
FEATURE                   Location/Qualifiers
source                    1..358
                          mol_type = protein
                          organism = Teseptimavirus T7
MOD_RES                   73
                          note = Glutamic acid
SEQUENCE: 6
MNIKTNPFKA VSFVESAIKK ALDNAGYLIA EIKYDGVRGN ICVDNTANSY WLSRVSKTIP   60
ALEHLNGFDV RWERLLNDDR CFYKDGFMLD GELMVKGVDF NTGSGLLRTK WTDTKNQEFH  120
EELFVEPIRK KDKVPFKLHT GHLHIKLYAI LPLHIVESGE DCDVMTLLMQ EHVKNMLPLL  180
QEYFPEIEWQ AAESYEVYDM VELQQLYEQK RAEGHEGLIV KDPMCIYKRG KKSGWWKMKP  240
ENEADGIIQG LVWGTKGLAN EGKVIGFEVL LESGRLVNAT NISRALMDEF TETVKEATLS  300
QWGFFSPYGI GDNDACTINP YDGWACQISY MEETPDGSLR HPSFVMFRGT EDNPQEKM    358
```

```
SEQ ID NO: 7              moltype = AA  length = 358
FEATURE                   Location/Qualifiers
source                    1..358
                          mol_type = protein
                          organism = Teseptimavirus T7
MOD_RES                   137
                          note = Glutamic acid
SEQUENCE: 7
MNIKTNPFKA VSFVESAIKK ALDNAGYLIA EIKYDGVRGN ICVDNTANSY WLSRVSKTIP   60
ALKHLNGFDV RWKRLLNDDR CFYKDGFMLD GELMVKGVDF NTGSGLLRTK WTDTKNQEFH  120
EELFVEPIRK KDKVPFELHT GHLHIKLYAI LPLHIVESGE DCDVMTLLMQ EHVKNMLPLL  180
QEYFPEIEWQ AAESYEVYDM VELQQLYEQK RAEGHEGLIV KDPMCIYKRG KKSGWWKMKP  240
ENEADGIIQG LVWGTKGLAN EGKVIGFEVL LESGRLVNAT NISRALMDEF TETVKEATLS  300
QWGFFSPYGI GDNDACTINP YDGWACQISY MEETPDGSLR HPSFVMFRGT EDNPQEKM    358
```

```
SEQ ID NO: 8              moltype = DNA  length = 1077
FEATURE                   Location/Qualifiers
```

-continued

```
source                  1..1077
                        mol_type = genomic DNA
                        note = DNA sequence of T7 DNA Ligase K174E
                        organism = Teseptimavirus T7
SEQUENCE: 8
atgaatatca agactaatcc gtttaaagca gtatcgttcg tggaaagcgc gatcaaaaaa    60
gccttggaca acgctggtta tttaatcgca gaaattaaat atgatggtgt cagagggaac   120
atctgcgtcg ataatacggc caattcgtat tggctgagcc gtgtgtctaa aactattccg   180
gcactcgaac acctgaatgg ttttgatgtt agatggaaac gccttttaaa tgacgatcgg   240
tgtttttaca aagatggctt tatgctggat ggggaactga tggttaaagg cgtcgatttc   300
aataccggat ctgggttatt acgtacgaaa tggactgaca caaaaaatca agaatttcac   360
gaagaattat ttgtagaacc aattcgaaaa aaggataaag tgcctttaa gttacataca    420
ggccatctgc atataaagct ctatgcgata ctgcccttc acattgtgga aagcggtgag    480
gattgtgacg tcatgacgct gctgatgcag aacatgtga aaacatgtt acctctgtta     540
caagaatatt ttccagagat tgagtggcag gccgcggaat cctatgaagt ttatgacatg    600
gtagaactcc agcagttgta tgaacaaaaa cgcgccgaag ggcacgaagg attgatcgtc    660
aaagatccca tgtgtatcta taaacggggt aaaaaatccg gttggtggaa aatgaaaccg    720
gaaaacgaag cggatggtat aattcaggga ctggtgtgg gtacgaaagg attagcgaat     780
gaaggcaaag tcatcggttt tgaagttttg ctggaaagcg gtcgcctcgt caatgcgaca    840
aacatcagtc gggcactgat ggatgagttc acagagaccg tgaaagaagc gaccttgtct    900
cagtggggct tcttttctcc ttacggtata ggagataatg atgcttgtac tattaatccg    960
tatgacggat gggcatgtca gatcagttac atggaagaaa ctcctgacgg ttcactcgcg   1020
catcccagct tcgtgatgtt ccgggggtact gaagataatc cccaagagaa aatgtaa     1077

SEQ ID NO: 9             moltype = AA   length = 358
FEATURE                 Location/Qualifiers
source                  1..358
                        mol_type = protein
                        organism = Teseptimavirus T7
MOD_RES                 174
                        note = Glutamic acid
SEQUENCE: 9
MNIKTNPFKA VSFVESAIKK ALDNAGYLIA EIKYDGVRGN ICVDNTANSY WLSRVSKTIP    60
ALEHLNGFDV RWKRLLNDDR CFYKDGFMLD GELMVKGVDF NTGSGLLRTK WTDTKNQEFH   120
EELFVEPIRK KDKVPFKLHT GHLHIKLYAI LPLHIVESGE DCDVMTLLMQ EHVENMLPLL   180
QEYFPEIEWQ AAESYEVYDM VELQQLYEQK RAEGHEGLIV KDPMCIYKRG KKSGWWKMKP   240
ENEADGIIQG LVWGTKGLAN EGKVIGFEVL LESGRLVNAT NISRALMDEF TETVKEATLS   300
QWGFFSPYGI GDNDACTINP YDGWACQISY MEETPDGSLR HPSFVMFRGT EDNPQEKM     358

SEQ ID NO: 10           moltype = DNA   length = 1077
FEATURE                 Location/Qualifiers
source                  1..1077
                        mol_type = genomic DNA
                        organism = Teseptimavirus T7
SEQUENCE: 10
atgaatatca agactaatcc gtttaaagca gtatcgttcg tggaaagcgc gatcaaaaaa    60
gccttggaca acgctggtta tttaatcgca gaaattaaat atgatggtgt cagagggaac   120
atctgcgtcg ataatacggc caattcgtat tggctgagcc gtgtgtctaa aactattccg   180
gcactcgaac acctgaatgg ttttgatgtt agatggaaac gccttttaaa tgacgatcgg   240
tgtttttaca aagatggctt tatgctggat ggggaactga tggttaaagg cgtcgatttc   300
aataccggat ctgggttatt acgtacgaaa tggactgaca caaaaaatca agaatttcac   360
gaagaattat ttgtagaacc aattcgaaaa aaggataaag tgcctttaa gttacataca    420
ggccatctgc atataaagct ctatgcgata ctgcccttc acattgtgga aagcggtgag    480
gattgtgacg tcatgacgct gctgatgcag aacatgtga aaacatgtt acctctgtta     540
caaaaatatt ttccagagat tgagtggcag gccgcggaat cctatgaagt ttatgacatg    600
gtagaactcc agcagttgta tgaacaaaaa cgcgccgaag ggcacgaagg attgatcgtc    660
aaagatccca tgtgtatcta taaacggggt aaaaaatccg gttggtggaa aatgaaaccg    720
gaaaacgaag cggatggtat aattcaggga ctggtgtggg gtacgaaagg attagcgaat    780
gaaggcaaag tcatcggttt tgaagttttg ctggaaagcg gtcgcctcgt caatgcgaca    840
aacatcagtc gggcactgat ggatgagttc acagagaccg tgaaagaagc gaccttgtct    900
cagtggggct tcttttctcc ttacggtata ggagataatg atgcttgtac tattaatccg    960
tatgacggat gggcatgtca gatcagttac atggaagaaa ctcctgacgg ttcactcgcg   1020
catcccagct tcgtgatgtt ccggggtact gaagataatc cccaagagaa aatgtaa     1077

SEQ ID NO: 11           moltype = AA   length = 358
FEATURE                 Location/Qualifiers
source                  1..358
                        mol_type = protein
                        organism = Teseptimavirus T7
MOD_RES                 182
                        note = Lysin
SEQUENCE: 11
MNIKTNPFKA VSFVESAIKK ALDNAGYLIA EIKYDGVRGN ICVDNTANSY WLSRVSKTIP    60
ALEHLNGFDV RWKRLLNDDR CFYKDGFMLD GELMVKGVDF NTGSGLLRTK WTDTKNQEFH   120
EELFVEPIRK KDKVPFKLHT GHLHIKLYAI LPLHIVESGE DCDVMTLLMQ EHVKNMLPLL   180
QKYFPEIEWQ AAESYEVYDM VELQQLYEQK RAEGHEGLIV KDPMCIYKRG KKSGWWKMKP   240
ENEADGIIQG LVWGTKGLAN EGKVIGFEVL LESGRLVNAT NISRALMDEF TETVKEATLS   300
QWGFFSPYGI GDNDACTINP YDGWACQISY MEETPDGSLR HPSFVMFRGT EDNPQEKM     358
```

-continued

```
SEQ ID NO: 12          moltype = DNA   length = 1077
FEATURE                Location/Qualifiers
source                 1..1077
                       mol_type = other DNA
                       note = DNA sequence of T7 DNA Ligase K210E
                       organism = Teseptimavirus T7
SEQUENCE: 12
atgaatatca agactaatcc gtttaaagca gtatcgttcg tggaaagcgc gatcaaaaaa    60
gccttggaca acgctggtta tttaatcgca gaaattaaat atgatggtgt cagagggaac   120
atctcgtcg ataatacggc caattcgtat tggctgagcc gtgtgtctaa aactattccg    180
gcactcgaac acctgaatgg ttttgatgtt agatggaaac gccttttaaa tgacgatcgg   240
tgttttaca aagatggctt tatgctggat ggggaactga tggttaaagg cgtcgatttc    300
aataccggat ctgggttatt acgtacgaaa tggactgaca caaaaaatca agaatttcac   360
gaagaattat ttgtagaacc aattcgaaaa aaggataaag tgcctttaa gttacataca    420
ggccatctgc atataaagct ctatgcgata ctgcccttc acattgtgga aagcggtgag    480
gattgtgacg tcatgacgct gctgatgcag gaacatgtga aaaacatgtt acctctgtta   540
caagaatatt ttccagagat tgagtggcag gccgcggaat cctatgaagt ttatgacatg    600
gtagaactcc agcagttgta tgaacagaaa cgcgccgaag ggcacgaagg attgatcgtc    660
aaagatccca tgtgtatcta taaacggggt aaaaaatccg gttggtggaa aatgaaaccg    720
gaaaacgaag cggatggtat aattcaggga ctggtgtggg gtacgaaagg attagcgaat    780
gaaggcaaag tcatcggttt tgaagttttg ctggaaagcg gtcgcctcgt caatgcgaca    840
aacatcagtc gggcactgat ggatgagttc acagagacca tgaaagaagc gaccttgtct    900
cagtgggggct tctttctcc ttacggtata ggagataatg atgcttgtac tattaatccg    960
tatgacggat gggcatgtca gatcagttac atggaagaaa ctcctgacgg ttcactgcgc   1020
catcccagct tcgtgatgtt ccggggtact gaagataatc cccaagagaa aatgtaa       1077

SEQ ID NO: 13          moltype = AA   length = 358
FEATURE                Location/Qualifiers
source                 1..358
                       mol_type = protein
                       organism = Teseptimavirus T7
MOD_RES                210
                       note = Glutamic acid
SEQUENCE: 13
MNIKTNPFKA VSFVESAIKK ALDNAGYLIA EIKYDGVRGN ICVDNTANSY WLSRVSKTIP     60
ALEHLNGFDV RWKRLLNDDR CFYKDGFMLD GELMVKGVDF NTGSGLLRTK WTDTKNQEFH    120
EELFVEPIRK KDKVPFKLHT GHLHIKLYAI LPLHIVESGE DCDVMTLLMQ EHVKNMLPLL    180
QEYFPEIEWQ AAESYEVYDM VELQQLYEQE RAEGHEGLIV KDPMCIYKRG KKSGWWKMKP    240
ENEADGIIQG LVWGTKGLAN EGKVIGFEVL LESGRLVNAT NISRALMDEF TETVKEATLS    300
QWGFFSPYGI GDNDACTINP YDGWACQISY MEETPDGSLR HPSFVMFRGT EDNPQEKM      358

SEQ ID NO: 14          moltype = DNA   length = 1077
FEATURE                Location/Qualifiers
source                 1..1077
                       mol_type = genomic DNA
                       note = DNA sequence of T7 DNA Ligase E243K
                       organism = Teseptimavirus T7
SEQUENCE: 14
atgaatatca agactaatcc gtttaaagca gtatcgttcg tggaaagcgc gatcaaaaaa    60
gccttggaca acgctggtta tttaatcgca gaaattaaat atgatggtgt cagagggaac   120
atctcgtcg ataatacggc caattcgtat tggctgagcc gtgtgtctaa aactattccg    180
gcactcgaac acctgaatgg ttttgatgtt agatggaaac gccttttaaa tgacgatcgg   240
tgttttaca aagatggctt tatgctggat ggggaactga tggttaaagg cgtcgatttc    300
aataccggat ctgggttatt acgtacgaaa tggactgaca caaaaaatca agaatttcac   360
gaagaattat ttgtagaacc aattcgaaaa aaggataaag tgcctttaa gttacataca    420
ggccatctgc atataaagct ctatgcgata ctgcccttc acattgtgga aagcggtgag    480
gattgtgacg tcatgacgct gctgatgcag gaacatgtga aaaacatgtt acctctgtta   540
caagaatatt ttccagagat tgagtggcag gccgcggaat cctatgaagt ttatgacatg    600
gtagaactcc agcagttgta tgaacaaaaa cgcgccgaag ggcacgaagg attgatcgtc    660
aaagatccca tgtgtatcta taaacggggt aaaaaatccg gttggtggaa aatgaaaccg    720
gaaaacaaag cggatggtat aattcaggga ctggtgtggg gtacgaaagg attagcgaat    780
gaaggcaaag tcatcggttt tgaagttttg ctggaaagcg gtcgcctcgt caatgcgaca    840
aacatcagtc gggcactgat ggatgagttc acagagaccg tgaaagaagc gaccttgtct    900
cagtgggggct tctttctcc ttacggtata ggagataatg atgcttgtac tattaatccg    960
tatgacggat gggcatgtca gatcagttac atggaagaaa ctcctgacgg ttcactgcgc   1020
catcccagct tcgtgatgtt ccggggtact gaagataatc cccaagagaa aatgtaa       1077

SEQ ID NO: 15          moltype = AA   length = 358
FEATURE                Location/Qualifiers
source                 1..358
                       mol_type = protein
                       organism = Teseptimavirus T7
MOD_RES                243
                       note = Lysin
SEQUENCE: 15
MNIKTNPFKA VSFVESAIKK ALDNAGYLIA EIKYDGVRGN ICVDNTANSY WLSRVSKTIP     60
ALEHLNGFDV RWKRLLNDDR CFYKDGFMLD GELMVKGVDF NTGSGLLRTK WTDTKNQEFH    120
EELFVEPIRK KDKVPFKLHT GHLHIKLYAI LPLHIVESGE DCDVMTLLMQ EHVKNMLPLL    180
QEYFPEIEWQ AAESYEVYDM VELQQLYEQK RAEGHEGLIV KDPMCIYKRG KKSGWWKMKP    240
```

-continued

```
ENKADGIIQG LVWGTKGLAN EGKVIGFEVL LESGRLVNAT NISRALMDEF TETVKEATLS  300
QWGFFSPYGI GDNDACTINP YDGWACQISY MEETPDGSLR HPSFVMFRGT EDNPQEKM     358

SEQ ID NO: 16            moltype = DNA   length = 1077
FEATURE                  Location/Qualifiers
source                   1..1077
                         mol_type = genomic DNA
                         note = DNA sequence of T7 DNA Ligase D245R
                         organism = Teseptimavirus T7
SEQUENCE: 16
atgaatatca agactaatcc gtttaaagca gtatcgttcg tggaaagcgc gatcaaaaaa   60
gccttggaca cgctggtta tttaatcgca gaaattaaat atgatggtgt cagagggaac  120
atctgcgtcg ataatacggc caattcgtat tggctgagcc gtgtgtctaa aactattccg  180
gcactcgaac acctgaatgg ttttgatgtt agatggaac gccttttaaa tgacgatcgg  240
tgttttaca aagatggctt tatgctggat ggggaactga tggttaaagg cgtcgatttc  300
aataccggat ctgggttatt acgtacgaaa tggactgaca caaaaaatca agaatttcac  360
gaagaattat ttgtagaacc aattcgaaaa aaggataaag tgccttttaa gttacataca  420
ggccatctgc atataaagct ctatgcgata ctgcccttc acattgtgga aagcggtcag  480
gattgtgacg tcatgacgct gctgatgcag aacatgtga aaaacatgtt acctctgtta  540
caagaatatt ttccagagat tgagtggcag gccgcggaat cctatgaagt ttatgacatg  600
gtagaactcc agcagttgta tgaacaaaaa cgcgccgaag gcacgaagg attgatcgtc  660
aaagatccca tgtgtatcta taaacggggt aaaaaatccg gttggtggaa aatgaaaccg  720
gaaaacgaag cgcgtggtat aattcaggga ctggtgtggg gtacgaaagg attagcgaat  780
gaaggcaaag tcatcggttt tgaagttttg ctggaaagcg gtcgcctcgt caatgcgaca  840
aacatcagtc gggcactgat ggatgagttc acagagaccg tgaaagaagc gaccttgtct  900
cagtggggct tcttttctcc ttacggtata ggagataatg atgcttgtac tattaatccg  960
tatgacggat gggcatgtca gatcagttac atggaagaaa ctcctgacgg ttcactgcgc  1020
catcccagct tcgtgatgtt ccggggtact gaagataatc cccaagagaa aatgtaa    1077

SEQ ID NO: 17            moltype = AA   length = 358
FEATURE                  Location/Qualifiers
source                   1..358
                         mol_type = protein
                         organism = Teseptimavirus T7
MOD_RES                  245
                         note = Arginine
SEQUENCE: 17
MNIKTNPFKA VSFVESAIKK ALDNAGYLIA EIKYDGVRGN ICVDNTANSY WLSRVSKTIP   60
ALEHLNGFDV RWKRLLNDDR CFYKDGFMLD GELMVKGVDF NTGSGLLRTK WTDTKNQEFH  120
EELFVEPIRK KDKVPFKLHT GHLHIKLYAI LPLHIVESGE DCDVMTLLMQ EHVKNMLPLL  180
QEYFPEIEWQ AAESYEVYDM VELQQLYEQK RAEGHEGLIV KDPMCIYKRG KKSGWWKMKP  240
ENEARGIIQG LVWGTKGLAN EGKVIGFEVL LESGRLVNAT NISRALMDEF TETVKEATLS  300
QWGFFSPYGI GDNDACTINP YDGWACQISY MEETPDGSLR HPSFVMFRGT EDNPQEKM     358

SEQ ID NO: 18            moltype = DNA   length = 1077
FEATURE                  Location/Qualifiers
source                   1..1077
                         mol_type = genomic DNA
                         note = DNA sequence of T7 DNA Ligase E268K
                         organism = Teseptimavirus T7
SEQUENCE: 18
atgaatatca agactaatcc gtttaaagca gtatcgttcg tggaaagcgc gatcaaaaaa   60
gccttggaca cgctggtta tttaatcgca gaaattaaat atgatggtgt cagagggaac  120
atctgcgtcg ataatacggc caattcgtat tggctgagcc gtgtgtctaa aactattccg  180
gcactcgaac acctgaatgg ttttgatgtt agatggaac gccttttaaa tgacgatcgg  240
tgttttaca aagatggctt tatgctggat ggggaactga tggttaaagg cgtcgatttc  300
aataccggat ctgggttatt acgtacgaaa tggactgaca caaaaaatca agaatttcac  360
gaagaattat ttgtagaacc aattcgaaaa aaggataaag tgccttttaa gttacataca  420
ggccatctgc atataaagct ctatgcgata ctgcccttc acattgtgga aagcggtgag  480
gattgtgacg tcatgacgct gctgatgcag aacatgtga aaaacatgtt acctctgtta  540
caagaatatt ttccagagat tgagtggcag gccgcggaat cctatgaagt ttatgacatg  600
gtagaactcc agcagttgta tgaacaaaaa cgcgccgaag gcacgaagg attgatcgtc  660
aaagatccca tgtgtatcta taaacggggt aaaaaatccg gttggtggaa aatgaaaccg  720
gaaaacgaag cggatggtat aattcaggga ctggtgtggg gtacgaaagg attagcgaat  780
gaaggcaaag tcatcggttt taaagttttg ctggaaagcg gtcgcctcgt caatgcgaca  840
aacatcagtc gggcactgat ggatgagttc acagagaccg tgaaagaagc gaccttgtct  900
cagtggggct tcttttctcc ttacggtata ggagataatg atgcttgtac tattaatccg  960
tatgacggat gggcatgtca gatcagttac atggaagaaa ctcctgacgg ttcactgcgc  1020
catcccagct tcgtgatgtt ccggggtact gaagataatc cccaagagaa aatgtaa    1077

SEQ ID NO: 19            moltype = AA   length = 358
FEATURE                  Location/Qualifiers
source                   1..358
                         mol_type = protein
                         organism = Teseptimavirus T7
MOD_RES                  268
                         note = Lysin
SEQUENCE: 19
MNIKTNPFKA VSFVESAIKK ALDNAGYLIA EIKYDGVRGN ICVDNTANSY WLSRVSKTIP   60
```

```
ALEHLNGFDV RWKRLLNDDR CFYKDGFMLD GELMVKGVDF NTGSGLLRTK WTDTKNQEFH   120
EELFVEPIRK KDKVPFKLHT GHLHIKLYAI LPLHIVESGE DCDVMTLLMQ EHVKNMLPLL   180
QEYFPEIEWQ AAESYEVYDM VELQQLYEQK RAEGHEGLIV KDPMCIYKRG KKSGWWKMKP   240
ENEADGIIQG LVWGTKGLAN EGKVIGFKVL LESGRLVNAT NISRALMDEF TETVKEATLS   300
QWGFFSPYGI GDNDACTINP YDGWACQISY MEETPDGSLR HPSFVMFRGT EDNPQEKM     358

SEQ ID NO: 20          moltype = DNA   length = 1077
FEATURE                Location/Qualifiers
source                 1..1077
                       mol_type = genomic DNA
                       note = DNA sequence of T7 DNA Ligase E272K
                       organism = Teseptimavirus T7
SEQUENCE: 20
atgaatatca agactaatcc gtttaaagca gtatcgttcg tggaaagcgc gatcaaaaaa   60
gccttggaca acgctggtta tttaatcgca gaaattaaat atgatggtgt cagagggaac   120
atctgcgtcg ataatacggc caattcgtat tggctgagcc gtgtgtctaa aactattccg   180
gcactcgaac acctgaatgg ttttgatgtt agatggaaac gcctttttaaa tgacgatcgg   240
tgtttttaca aagatggctt tatgctggat ggggaactga tggttaaagg cgtcgatttc   300
aataccggat ctgggttatt acgtacgaaa tggactgaca caaaaaatca agaatttcac   360
gaagaattat ttgtagaacc aattcgaaaa aggataaag tgccttttaa gttacataca   420
ggccatctgc atataaagct ctatgcgata ctgcccttc acattgtgga aagcggtgag   480
gattgtgacg tcatgacgct gctgatgcag aacatgtga aaaacatgtt acctctgtta   540
caagaatatt ttccagagat tgagtggcag gccgcggaat cctatgaagt ttatgacatg   600
gtagaactcc agcagttgta tgaacaaaaa cgcgccgaag ggcacgaagg attgatcgtc   660
aaagatccca tgtgtatcta taaacggggt aaaaaatccg gttggtggaa aatgaaaccg   720
gaaaacgaag cggatggtat aattcaggga ctggtgtggg gtacgaaagg attagcgaat   780
gaaggcaaag tcatcggttt tgaagttttg ctgaaaagcg gtcgcctcgt caatgcgaca   840
aacatcagtc gggcactgat ggatgagttc acagagaccg tgaaagaagc gaccttgtct   900
cagtggggct tcttttctcc ttacggtata ggagataatg atgcttgtac tattaatccg   960
tatgacggat gggcatgtca gatcagttac atggaagaaa ctcctgacgg ttcactcgcg   1020
catcccagct tcgtgatgtt ccggggtact gaagataatc cccaagagaa aatgtaa     1077

SEQ ID NO: 21          moltype = AA   length = 358
FEATURE                Location/Qualifiers
source                 1..358
                       mol_type = protein
                       organism = Teseptimavirus T7
MOD_RES                272
                       note = Lysin
SEQUENCE: 21
MNIKTNPFKA VSFVESAIKK ALDNAGYLIA EIKYDGVRGN ICVDNTANSY WLSRVSKTIP   60
ALEHLNGFDV RWKRLLNDDR CFYKDGFMLD GELMVKGVDF NTGSGLLRTK WTDTKNQEFH   120
EELFVEPIRK KDKVPFKLHT GHLHIKLYAI LPLHIVESGE DCDVMTLLMQ EHVKNMLPLL   180
QEYFPEIEWQ AAESYEVYDM VELQQLYEQK RAEGHEGLIV KDPMCIYKRG KKSGWWKMKP   240
ENEADGIIQG LVWGTKGLAN EGKVIGFEVL LKSGRLVNAT NISRALMDEF TETVKEATLS   300
QWGFFSPYGI GDNDACTINP YDGWACQISY MEETPDGSLR HPSFVMFRGT EDNPQEKM     358

SEQ ID NO: 22          moltype = DNA   length = 1077
FEATURE                Location/Qualifiers
source                 1..1077
                       mol_type = genomic DNA
                       note = DNA sequence of T7 DNA Ligase E289K
                       organism = Teseptimavirus T7
SEQUENCE: 22
atgaatatca agactaatcc gtttaaagca gtatcgttcg tggaaagcgc gatcaaaaaa   60
gccttggaca acgctggtta tttaatcgca gaaattaaat atgatggtgt cagagggaac   120
atctgcgtcg ataatacggc caattcgtat tggctgagcc gtgtgtctaa aactattccg   180
gcactcgaac acctgaatgg ttttgatgtt agatggaaac gcctttttaaa tgacgatcgg   240
tgtttttaca aagatggctt tatgctggat ggggaactga tggttaaagg cgtcgatttc   300
aataccggat ctgggttatt acgtacgaaa tggactgaca caaaaaatca agaatttcac   360
gaagaattat ttgtagaacc aattcgaaaa aggataaag tgccttttaa gttacataca   420
ggccatctgc atataaagct ctatgcgata ctgcccttc acattgtgga aagcggtgag   480
gattgtgacg tcatgacgct gctgatgcag aacatgtga aaaacatgtt acctctgtta   540
caagaatatt ttccagagat tgagtggcag gccgcggaat cctatgaagt ttatgacatg   600
gtagaactcc agcagttgta tgaacaaaaa cgcgccgaag ggcacgaagg attgatcgtc   660
aaagatccca tgtgtatcta taaacggggt aaaaaatccg gttggtggaa aatgaaaccg   720
gaaaacgaag cggatggtat aattcaggga ctggtgtggg gtacgaaagg attagcgaat   780
gaaggcaaag tcatcggttt tgaagttttg ctgaaaagcg gtcgcctcgt caatgcgaca   840
aacatcagtc gggcactgat ggataagttc acagagaccg tgaaagaagc gaccttgtct   900
cagtggggct tcttttctcc ttacggtata ggagataatg atgcttgtac tattaatccg   960
tatgacggat gggcatgtca gatcagttac atggaagaaa ctcctgacgg ttcactcgcg   1020
catcccagct tcgtgatgtt ccggggtact gaagataatc cccaagagaa aatgtaa     1077

SEQ ID NO: 23          moltype = AA   length = 358
FEATURE                Location/Qualifiers
source                 1..358
                       mol_type = protein
                       organism = Teseptimavirus T7
MOD_RES                289
```

-continued

```
                              note = Lysin
SEQUENCE: 23
MNIKTNPFKA VSFVESAIKK ALDNAGYLIA EIKYDGVRGN ICVDNTANSY WLSRVSKTIP   60
ALEHLNGFDV RWKRLLNDDR CFYKDGFMLD GELMVKGVDF NTGSGLLRTK WTDTKNQEFH  120
EELFVEPIRK KDKVPFKLHT GHLHIKLYAI LPLHIVESGE DCDVMTLLMQ EHVKNMLPLL  180
QEYFPEIEWQ AAESYEVYDM VELQQLYEQK RAEGHEGLIV KDPMCIYKRG KKSGWWKMKP  240
ENEADGIIQG LVWGTKGLAN EGKVIGFEVL LESGRLVNAT NISRALMDKF TETVKEATLS  300
QWGFFSPYGI GDNDACTINP YDGWACQISY MEETPDGSLR HPSFVMFRGT EDNPQEKM    358

SEQ ID NO: 24              moltype = DNA  length = 1077
FEATURE                    Location/Qualifiers
source                     1..1077
                           mol_type = genomic DNA
                           note = DNA sequence of T7 DNA Ligase K295E
                           organism = Teseptimavirus T7

SEQUENCE: 24
atgaatatca agactaatcc gtttaaagca gtatcgttcg tggaaagcgc gatcaaaaaa   60
gccttggaca acgctggtta tttaatcgca gaaattaaat atgatggtgt cagagggaac  120
atctgcgtcg ataatacggc caattcgtat tggctgagcc gtgtgtctaa aactattccg  180
gcactcgaac acctgaatgg ttttgatgtt agatggaaac gccttttaaa tgacgatcgg  240
tgttttttaca aagatggctt tatgctggat ggggaactga tggttaaagg cgtcgatttc  300
aataccggat ctgggttatt acgtacgaaa tggactgaca caaaaaatca agaatttcac  360
gaagaattat ttgtagaacc aattcgaaaa aaggataaag tgcctttaa gttacataca   420
ggccatctgc atataaagct ctatgcgata ctgcccttc acattgtgga aagcggtgag   480
gattgtgacg tcatgacgct gctgatgcag gaacatgtga aaaacatgtt acctctgtta  540
caagaatatt ttccagagat tgagtggcag gccgcgaat cctatgaagt ttatgacatg   600
gtagaactcc agcagttgta tgaacaaaaa cgcgccgaag ggcacgaagg attgatcgtc  660
aaagatccca tgtgtatcta taaacgaggt aaaaaatccg gttggtggaa aatgaaaccg  720
gaaaacgaag cggatggtat aattcaggga ctggtgtggg gtacgaaagg attagcgaat  780
gaaggcaaag tcatcggttt tgaagttttg ctggaaagcg gtcgcctcgt caatgcgaca  840
aacatcagtc gggcactgat ggatgagttc acagagaccg tggaagaagc gaccttgtct  900
cagtggggct tcttttctcc ttacggtata ggagataatg atgcttgtac tattaatccg  960
tatgacggat gggcatgtca gatcagttac atggaagaaa ctcctgacgg ttcactgcgc 1020
catcccagct tcgtgatgtt ccggggtact gaagataatc cccaagagaa aatgtaa    1077

SEQ ID NO: 25              moltype = AA  length = 358
FEATURE                    Location/Qualifiers
source                     1..358
                           mol_type = protein
                           organism = Teseptimavirus T7
MOD_RES                    295
                           note = Glutamic Acid
SEQUENCE: 25
MNIKTNPFKA VSFVESAIKK ALDNAGYLIA EIKYDGVRGN ICVDNTANSY WLSRVSKTIP   60
ALEHLNGFDV RWKRLLNDDR CFYKDGFMLD GELMVKGVDF NTGSGLLRTK WTDTKNQEFH  120
EELFVEPIRK KDKVPFKLHT GHLHIKLYAI LPLHIVESGE DCDVMTLLMQ EHVKNMLPLL  180
QEYFPEIEWQ AAESYEVYDM VELQQLYEQK RAEGHEGLIV KDPMCIYKRG KKSGWWKMKP  240
ENEADGIIQG LVWGTKGLAN EGKVIGFEVL LESGRLVNAT NISRALMDEF TETVEKATLS  300
QWGFFSPYGI GDNDACTINP YDGWACQISY MEETPDGSLR HPSFVMFRGT EDNPQEKM    358

SEQ ID NO: 26              moltype = DNA  length = 1077
FEATURE                    Location/Qualifiers
source                     1..1077
                           mol_type = genomic DNA
                           note = DNA sequence of T7 DNA Ligase and D336R
                           organism = Teseptimavirus T7

SEQUENCE: 26
atgaatatca agactaatcc gtttaaagca gtatcgttcg tggaaagcgc gatcaaaaaa   60
gccttggaca acgctggtta tttaatcgca gaaattaaat atgatggtgt cagagggaac  120
atctgcgtcg ataatacggc caattcgtat tggctgagcc gtgtgtctaa aactattccg  180
gcactcgaac acctgaatgg ttttgatgtt agatggaaac gccttttaaa tgacgatcgg  240
tgttttttaca aagatggctt tatgctggat ggggaactga tggttaaagg cgtcgatttc  300
aataccggat ctgggttatt acgtacgaaa tggactgaca caaaaaatca agaatttcac  360
gaagaattat ttgtagaacc aattcgaaaa aaggataaag tgcctttaa gttacataca   420
ggccatctgc atataaagct ctatgcgata ctgcccttc acattgtgga aagcggtgag   480
gattgtgacg tcatgacgct gctgatgcag gaacatgtga aaaacatgtt acctctgtta  540
caagaatatt ttccagagat tgagtggcag gccgcgaat cctatgaagt ttatgacatg   600
gtagaactcc agcagttgta tgaacaaaaa cgcgccgaag ggcacgaagg attgatcgtc  660
aaagatccca tgtgtatcta taaacgaggt aaaaaatccg gttggtggaa aatgaaaccg  720
gaaaacgaag cggatggtat aattcaggga ctggtgtggg gtacgaaagg attagcgaat  780
gaaggcaaag tcatcggttt tgaagttttg ctggaaagcg gtcgcctcgt caatgcgaca  840
aacatcagtc gggcactgat ggatgagttc acagagaccg tgaagaagc gaccttgtct   900
cagtggggct tcttttctcc ttacggtata ggagataatg atgcttgtac tattaatccg  960
tatgacggat gggcatgtca gatcagttac atggaagaaa ctcctcgtgg ttcactgcgc 1020
catcccagct tcgtgatgtt ccggggtact gaagataatc cccaagagaa aatgtaa    1077

SEQ ID NO: 27              moltype = AA  length = 358
FEATURE                    Location/Qualifiers
source                     1..358
```

-continued

```
                          mol_type = protein
                          organism = Teseptimavirus T7
MOD_RES                   336
                          note = Arginine
SEQUENCE: 27
MNIKTNPFKA VSFVESAIKK ALDNAGYLIA EIKYDGVRGN ICVDNTANSY WLSRVSKTIP  60
ALEHLNGFDV RWKRLLNDDR CFYKDGFMLD GELMVKGVDF NTGSGLLRTK WTDTKNQEFH 120
EELFVEPIRK KDKVPFKLHT GHLHIKLYAI LPLHIVESGE DCDVMTLLMQ EHVKNMLPLL 180
QEYFPEIEWQ AAESYEVYDM VELQQLYEQK RAEGHEGLIV KDPMCIYKRG KKSGWWKMKP 240
ENEADGIIQG LVWGTKGLAN EGKVIGFEVL LESGRLVNAT NISRALMDEF TETVKEATLS 300
QWGFFSPYGI GDNDACTINP YDGWACQISY MEETPRGSLR HPSFVMFRGT EDNPQEKM   358
```